(12) United States Patent
Kunz et al.

(10) Patent No.: US 10,662,167 B2
(45) Date of Patent: May 26, 2020

(54) HMF PRODUCTION METHOD

(71) Applicant: Südzucker AG, Mannheim (DE)

(72) Inventors: Markwart Kunz, Braunschweig (DE); Alireza Haji Begli, Ramsen (DE); Christine Kröner, Kindenheim (DE); Wolfgang Wach, Worms (DE); Alain-Michel Graf, Worms (DE); Wolfgang Kraus, Nussloch (DE)

(73) Assignee: SUDZUCKER AG, Mannheim (DE)

( * ) Notice: Subject to any disclaimer, the term of this patent is extended or adjusted under 35 U.S.C. 154(b) by 0 days.

(21) Appl. No.: 16/465,205

(22) PCT Filed: Dec. 1, 2017

(86) PCT No.: PCT/EP2017/081236
§ 371 (c)(1),
(2) Date: May 30, 2019

(87) PCT Pub. No.: WO2018/100184
PCT Pub. Date: Jun. 7, 2018

(65) Prior Publication Data
US 2020/0002300 A1    Jan. 2, 2020

(30) Foreign Application Priority Data

Dec. 2, 2016  (DE) .................. 10 2016 224 073

(51) Int. Cl.
*C07D 307/50*    (2006.01)
(52) U.S. Cl.
CPC .................. *C07D 307/50* (2013.01)
(58) Field of Classification Search
CPC .................................................. C07D 307/50
See application file for complete search history.

(56) References Cited

U.S. PATENT DOCUMENTS

| 4,740,605 A * | 4/1988 | Rapp ................... C07D 307/46 |
| | | 549/483 |
| 2011/0137084 A1 | 6/2011 | Berl et al. |
| 2014/0315262 A1 | 10/2014 | Sanborn et al. |
| 2015/0210661 A1 | 7/2015 | Boussie et al. |

FOREIGN PATENT DOCUMENTS

| DE | 3601281 A1 | 7/1987 |
| EP | 0230250 A2 | 7/1987 |
| EP | 0230250 B1 | 4/1991 |
| WO | WO-2013106136 A1 | 7/2013 |
| WO | WO-2015113060 A2 | 7/2015 |

OTHER PUBLICATIONS

International Search Report (in English and German) and Written Opinion (in German) issued in PCT/EP2017/081236, dated Feb. 23, 2018; ISA/EP.
International Preliminary Report on Patentability for corresponding International Application PCT/EP2017/081236. dated Jun. 4, 2019.
Rajendran et al.; J. Chromatogr. A 1216 (2009), pp. 709-738.

* cited by examiner

*Primary Examiner* — Timothy R Rozof
(74) *Attorney, Agent, or Firm* — Stephen T. Olson; Harness, Dickey & Pierce, P.L.C.

(57) ABSTRACT

The invention relates to a method for producing 5-hydroxymethylfurfural (HMF) in a continuous process, which leads to the obtainment of an HMF fraction, a carbohydrate/acid fraction, a fructose fraction, and a levulinic-acid and formic-acid fraction and advantageously makes it possible, because of the purity of the obtained fractions, to return the fructose fraction obtained by means of the method directly to the production process and to use the other fractions in further-processing processes without the need for complex, additional purification steps.

20 Claims, 10 Drawing Sheets

HMF PRODUCTION METHOD

CROSS-REFERENCE TO RELATED APPLICATIONS

This application is a 371 U.S. National Stage of International Application No. PCT/EP2017/081236, filed Dec. 1, 2017, which claims priority to German Patent Application No. 10 2016 224 073.0, filed Dec. 2, 2016. The entire disclosures of the above applications are incorporated herein by reference.

The present invention relates to a process for the production of 5-hydroxymethylfurfural (HMF) in a continuous process which results in obtaining an HMF fraction, a carbohydrate/acid fraction, a fructose fraction and a levulinic and formic acid fraction and, due to the purity of the fractions obtained, advantageously makes it possible for the fructose fraction obtained from the process to be returned directly to the production process and to use the further fractions without the need for expensive, additional purification steps in additional processes.

5-hydroxymethylfurfural (HMF) is a multifunctional molecule with a 5-ring aromatic system, an aldehyde and an alcohol group. The many functionalities make the molecule a versatile platform chemical which can be used as the basis for a wide variety of other compounds. The compounds that can be produced on the basis of HMF also include chemicals which are already produced on a mass scale by petrochemical means, for example caprolactam or adipic acid, but also compounds with a great potential for which no technical production process is available yet such as 2.5-furandicarboxylic acid (FDCA).

Despite the great potential of HMF and FDCA, there is still a lack of economical, technically established production processes for these compounds. The multifunctionality of HMF as one of the major advantages of the molecule has also proven to be a major drawback in terms of the resulting downstream chemistry that may be possible. HMF is not stable, especially in aqueous systems, under the reaction conditions required for the synthesis (acidic pH, increased temperature) and, on the one hand, reacts, when polymerized, with itself and/or the starting materials and intermediates to form so-called humins, which are soluble or insoluble depending on the chain length and lead to a brown to black coloration of the reaction solution. Another undesirable secondary reaction is the HMF acid hydrolysis to levulinic and formic acids, with in particular levulinic acid being able to react with HMF to form further undesired byproducts. For a most economical production of HMF, it is therefore essential to avoid the occurrence of this side reaction and the subsequent reaction of HMF and levulinic acid as much as possible.

Basically, in the many different synthetic routes described in prior art for the production of HMF, a distinction can be made between single-phase and two-phase reaction systems. Homogeneous and heterogeneous catalysts can be used in both approaches. In the case of single-phase systems, the HMF synthesis can be performed not only in purely aqueous systems but also in organic solvents such as DMSO, DMF and sulfolane, or in ionic liquids. Although the avoidance of aqueous systems leads to better selectivities for HMF based purely on the chemical reaction, high temperatures are often necessary to remove the solvents, under which, however, HMF may thermally decompose, which in turn significantly decreases the purity and yield of the HMF. In addition, when using anhydrous systems, the cost of solvents as well as safety and environmental considerations play a major role.

It is also disadvantageous that the hexoses used for the HMF synthesis, in particular fructose and/or glucose, have poor solubility in many common organic solvents.

In the two-phase reaction systems, the reaction of the hexose to HMF is carried out in the aqueous phase and the resulting HMF is extracted continuously by means of an organic solvent. In this case, the solvent must not be miscible with water and must have a sufficiently high partition coefficient for HMF between the aqueous and the organic phase in order to ensure an efficient extraction of the HMF. In particular, since the partition coefficients are not very high for most solvents, very large amounts of solvent often have to be used in such systems. The most commonly used organic solvent in two-phase reaction systems is methyl isobutyl ketone (MIBK), which is optionally used in combination with phase modifiers such as 2-butanol. However, as already shown for the single-phase anhydrous reaction systems, the final removal of the solvent(s) used in this case proves to be problematic because of the high boiling points of suitable solvents.

EP 0 230 250 B1 discloses processes for the production of 5-hydroxymethylfurfural including a crystalline product using water alone as the solvent. In the batch process described, saccharides are decomposed with an acidic catalyst in an aqueous solution at a temperature of approx. 100° C. to obtain a mixture of hexoses and HMF, and then the resulting HMF is separated from byproducts by means of ion exchange columns at a temperature ranging from 35 to 85° C., so that, in addition to an HMF fraction, a saccharide fraction can be obtained, which is available for a new HMF synthesis according to the method described. The batchwise conversion disclosed in this document is accompanied by a high fructose conversion and an immediately following high concentration of HMF in the reaction solution which, under the prevailing conditions, leads to an increased creation of byproducts and degradation products, which leads to a reduced HFM yield compared to the amount of fructose reacted.

WO 2013/106136 A1 relates to a process for the production of HMF and HMF derivatives from sugar, comprising the recovery of unreacted sugars, which are suitable for direct use in the fermentation of ethanol. In this case, hexose-containing solutions are reacted to HMF in the aqueous phase by means of an acid-catalyzed dehydration reaction, and then the unreacted sugar contained in the product mixture is separated from the product mixture by adsorption and/or solvent extraction, which is finally used in an aerobic or anaerobic fermentation process for the production of ethanol. It teaches the performance of the acid catalyzed dehydration reaction at a temperature of 175 to 205° C.

WO 2015/113060 A2 discloses the conversion of fructose-containing starting materials to HMF-containing products. By means of the process described, fructose, water, an acid catalyst and at least one other solvent are mixed in a reaction zone and brought to reaction by choosing suitable reaction parameters for a period of approximately 1 to 60 minutes, so that an HMF yield of 80% is not exceeded. Upon reaching the specified conversion, the reaction components are immediately cooled to minimize the creation of undesirable byproducts.

To ensure an economic and effective HMF production process, it is crucial that, during the conversion of a fructose-containing starting solution to HMF, the creation of undesirable byproducts and the decomposition of the HMF formed in the acid-catalyzed dehydration reaction is avoided as far as possible by choosing suitable reaction conditions and process steps and providing unreacted fructose separated from the interfering byproducts formed during the dehydration reaction, and thus in as pure a form as possible for the return to the continuous production process.

A corresponding method for the economic and effective production of HMF in a continuous process is hitherto unknown in the prior art.

It is therefore the object of the present invention to overcome the disadvantages and limitations known from the prior art, and, in particular, to provide a method for the conversion fructose in a highly-selective acid catalysis, and to avoid to the greatest extent possible any creation of byproducts, so as to make the conversion to HMF economic and effective.

The object of the present invention is achieved in particular by the technical teaching of the independent claims.

In particular, the present invention relates to a process for the production of 5-hydroxymethylfurfural (HMF) in a continuous process, comprising the following steps:

a) Provision of an aqueous fructose-containing starting solution and at least one homogeneous acidic catalyst,
b) Mixing of the aqueous fructose-containing starting solution and the at least one homogeneous acid catalyst to obtain a reaction solution having a carbohydrate content ranging from 5 wt % to 50 wt % (dry matter carbohydrate relative to the total weight of the reaction solution) and a fructose content ranging from 40 wt % to 100 wt % (dry matter fructose relative to the dry matter of the carbohydrates),
c) Feeding of the reaction solution obtained in step b) into a continuous reactor system and conversion of the fructose present in the reaction solution to HMF at a temperature ranging from 80° C. to 165° C. to obtain an HMF-containing product mixture while adjusting for a fructose conversion ranging from 1 mol % to 40 mol %,
d) Adjustment of the product mixture to a temperature ranging from 20° C. to 80° C., and
e) Purification of the product mixture obtained in step d) by using chromatography to separate at least four fractions comprising an HMF fraction, a carbohydrate/acid fraction, a fructose fraction and a levulinic and formic acid fraction.

In a preferred embodiment of the present invention, the above process for the production of 5-hydroxymethylfurfural (HMF) comprises in a further step f) the obtaining at least an HMF fraction, a carbohydrate/acid fraction, a fructose fraction and a levulinic and formic acid fraction.

In particular, the present invention relates to a process for the production of 5-hydroxymethylfurfural (HMF) in a continuous process, comprising the following steps:

a) Provision of an aqueous fructose-containing starting solution and at least one homogeneous acidic catalyst,
b) Mixing of the aqueous fructose-containing starting solution and the at least one homogeneous acid catalyst to obtain a reaction solution having a carbohydrate content ranging from 5 wt % to 50 wt % (dry matter carbohydrate relative to the total weight of the reaction solution) and a fructose content ranging from 40 wt % to 100 wt % (dry matter fructose relative to the dry matter of the carbohydrates),
c) Feeding of the reaction solution obtained in step b) into a continuous reactor system and conversion of the fructose present in the reaction solution to HMF at a temperature ranging from 80° C. to 165° C. to obtain an HMF-containing product mixture while adjusting for a fructose conversion ranging from 1 mol % to 40 mol %,
d) Adjustment of the product mixture to a temperature ranging from 20° C. to 80° C.,
e) Purification of the product mixture obtained in step d) by using chromatography to separate at least four fractions comprising an HMF fraction, a carbohydrate/acid fraction, a fructose fraction and a levulinic and formic acid fraction, and
f) Creation of at least an HMF fraction, a carbohydrate/acid fraction, a fructose fraction and a levulinic and formic acid fraction.

In a preferred embodiment, the present invention relates to a process for the production of 5-hydroxymethylfurfural (HMF) in a continuous process, comprising the following steps:

a) Provision of an aqueous fructose-containing starting solution, an aqueous recirculated fructose-containing fraction and at least one homogeneous acidic catalyst,
b) Mixing of the aqueous fructose-containing starting solution, the aqueous returned fructose-containing fraction and the at least on homogeneous acidic catalyst to obtain a reaction solution having a carbohydrate content ranging from 5 wt % to 50 wt % (dry matter carbohydrate relative to the total weight of the reaction solution) and a fructose content ranging from 40 wt % to 100 wt % (dry matter fructose relative to the dry matter of the carbohydrates),
c) Feeding of the reaction solution obtained in step b) into a continuous reactor system and conversion of the fructose present in the reaction solution to HMF at a temperature ranging from 80° C. to 165° C. to obtain an HMF-containing product mixture while adjusting for a fructose conversion ranging from 1 mol % to 40 mol %,
d) Adjustment of the product mixture to a temperature ranging from 20° C. to 80° C.,
e) Purification of the product mixture obtained in step d) using chromatography to separate at least four fractions comprising an HMF fraction, a carbohydrate/acid fraction, a fructose fraction and a levulinic and formic acid fraction, the obtained fructose fraction being continuously returned, at least partially, to step a).

In a preferred embodiment of the present invention, the above process for the production of 5-hydroxymethylfurfural (HMF) comprises in a further step f) the obtaining at least an HMF fraction, a carbohydrate/acid fraction, a fructose fraction and a levulinic and formic acid fraction, with the fructose fraction obtained being continuously, at least partially, returned to step a).

According to the invention, a process is provided which produces 5-hydroxymethylfurfural (HMF) in a continuous process through a selective, preferably highly selective, acid-catalyzed conversion of the fructose of an aqueous fructose-containing starting solution and, in a preferred embodiment, a returned fructose-containing fraction obtained from the process. According to the invention, the process according to the invention for the production of HMF is performed in such a way that, in the continuous reactor system used in step c), a limited conversion of the fructose ranging from 1 mol % to 40 mol % occurs due to an adjustment of the temperature, and preferably also the reaction time, by means of which a surprisingly high HMF selectivity can be achieved. After the limited fructose conversion of not more than 40 mol % has been achieved, the product mixture obtained in step d) is set to a temperature ranging from 20° C. to 80° C. so that the creation of undesirable byproducts and the decomposition of the HMF that was formed is largely prevented. In a subsequent step e), the HMF in the product mixture is separated from the other components of the product mixture by means of a chromatographic method, in particular a chromatography on ion exchange resins, in particular by cation exchange resins, in particular by means of single or multistage chromatography on ion exchange resins, in particular cation exchange resins. Preferably, in a step f) performed subsequently, i.e. after the chromatographic process has been completed, a carbohydrate/acid fraction, a fructose fraction and a levulinic and formic acid fraction are obtained, in particular isolated, in addition to the HMF fraction. Advantageously, the individual fractions obtained by means of the chromatographic method that is used have such high purities that they can be used directly, optionally after concentration, i.e. without further purification, in different subsequent processes.

According to the invention, the fructose fraction obtained is preferably substantially free, in particular completely free, of the levulinic acid that was created. According to the invention, the fructose fraction obtained is preferably substantially free, in particular completely free of the levulinic and formic acid that was created.

Levulinic acid disadvantageously promotes humic acid creation during the HMF synthesis. Thus, an increased content of levulinic acid in the reaction solution caused by the aqueous fructose fraction returned according to a preferred embodiment would lead to an increased creation of humic substances from HMF and carbohydrates and would thus significantly reduce the economic efficiency of the process. However, the fructose fraction separated in the process according to the invention in step e), and preferably obtained in step f), advantageously has such a high purity, and is in particular free of any levulinic acid, particularly preferably free of levulinic and formic acid, so that the fructose fraction can, in a preferred embodiment be returned to the process for further conversion, in particular step a) directly, optionally after concentration, in particular without purification steps. In particular, the limited conversion of fructose intended by the process according to the invention and the associated the reduced creation of byproducts and degradation products, in particular levulinic and formic acids as well as humic substances, and, in a preferred embodiment, through the return of a fraction of unreacted fructose separated from the product mixture, results in a high HMF selectivity and a high HMF yield.

According to the invention, the present process comprises the steps a) to e), preferably a) to f). In a preferred embodiment, therefore, the process may also comprise further process steps in addition to steps a) to e), particularly preferably a) to f), for example at least one filtration step, at least one decolorization and/or purification step, for example by means of activated carbon, and/or at least one concentration step. In a particularly preferred embodiment, the present process consists of the process steps a) to e), preferably a) to f). In a preferred embodiment, the process is carried out in the sequence of process steps a), b), c), d) and e), preferably a), b), c), d), e) and f).

According to the invention, the conversion of the fructose present in the reaction mixture to HMF in a continuous reactor system and the subsequent purification of the product mixture obtained by means of a chromatography for the separation of at least four fractions is performed continuously in the process for the production 5-hydroxymethylfurfural according to steps a) to e), preferably a) to f), that is the starting materials are continuously supplied and the products are continuously removed.

A continuous process according to the invention is preferably understood as a process in which not only the reactor system runs continuously, but the chromatographic purification as well.

According to the invention, the temperature used to carry out the process according to the invention in a preferred embodiment is always at the most 165° C., preferably at most 160° C., in particular at most 150° C.

The present invention makes it possible to provide processes for the production of HMF and/or formic acid and/or levulinic acid, in particular for the simultaneous production from a starting material, namely a fructose-containing starting solution and optionally a returned fructose-containing fraction.

The process according to the invention for the production of HMF in a preferred embodiment is therefore also a process for the production of HMF and formic acid and levulinic acid which comprises the steps a) to e), preferably a) to f), and which is used for the specific production of three products of interest.

The process according to the invention for the production of HMF in a preferred embodiment is therefore also a process for the production of HMF and formic acid, which comprises the steps a) to e), preferably a) to f), and which is used for the production of two valuable substances of interest.

The process according to the invention for the production of HMF in a preferred embodiment is therefore also a process for the production of HMF and levulinic acid, which comprises the steps a) to e), preferably a) to f), and which is used for the production of two valuable substances of interest.

Fructose/glucose syrups or fructose syrups are preferably used as the starting solution.

In a preferred embodiment of the present invention, at least one, preferably all, of the components provided in step a) are preheated to a temperature ranging from 50° C. to 165° C., preferably from 60° C. to 165° C., preferably from 70° C. to 165° C., preferably 80° C. to 165° C. before step b). In a preferred embodiment of the present invention, at least one, preferably all, of the components provided in step a) are preheated to a temperature ranging from 50° C. to 160° C., preferably 60° C. to 160° C., preferably 70° C. to 160° C., preferably 80° C. to 160° C. before step b). In a preferred embodiment of the present invention, at least one, preferably all, of the components provided in step a) are preheated to a temperature ranging from 50° C. to 150° C., preferably 60° C. to 150° C., preferably 70° C. to 150° C., preferably 80° C. to 150° C. before step b). Preferably, the reaction solution obtained in step b), preferably after step b) and before step c), is preheated to a temperature ranging from 50° C. to 165° C., preferably 60° C. to 165° C., preferably 70° C. to 165° C., preferably 80° C. to 165° C. Preferably, the reaction solution obtained in step b), preferably after step b) and before step c), is preheated to a temperature ranging from 50° C. to 160° C., preferably 60° C. to 160° C., preferably 70° C. to 160° C., preferably 80° C. to 160° C. Preferably, the reaction solution obtained in step b), preferably after step b) and before step c), is preheated to a temperature ranging from 50° C. to 150° C., preferably 60° C. to 150° C., preferably 70° C. to 150° C., preferably 80° C. to 150° C.

In a preferred embodiment of the present invention, the components provided in step a) are mixed in step b) to obtain a reaction solution having a carbohydrate content ranging from 5 wt % to 50 wt % (dry matter, hereinafter also referred to as DM, carbohydrate relative to the total weight of the reaction solution) and a fructose content ranging from 40 wt % to 100 wt % (dry matter fructose relative to the dry matter of the carbohydrates) and then reacted in the reactor according to process step c).

In a further preferred embodiment of the present invention, the aqueous fructose-containing starting solution provided in step a) and the optionally provided aqueous fructose-containing fraction that was returned is preheated before step b) to a temperature ranging from 50° C. to 165° C., preferably 60° C. to 165° C., preferably 70° C. to 165° C., preferably 80° C. to 165° C., preferably to a temperature ranging from 50° C. to 160° C., preferably 60° C. to 160° C., preferably 70° C. to 160° C., preferably 80° C. to 160° C., preferably to a temperature ranging from 50° C. to 150° C., preferably 60° C. to 150° C., preferably 70° C. to 150° C., preferably 80° C. to 150° C., and the at least one homogeneous acid catalyst, preferably at least one homogeneous mineral acid catalyst, is preheated separately before step b) to a temperature ranging from 50° C. to 165° C., preferably 60° C. to 165° C., preferably 70° C. to 165° C., preferably 80° C. to 165° C., preferably to a temperature ranging from 50° C. to 160° C., preferably 60° C. to 160° C., preferably 70° C. to 160° C., preferably 80° C. to 160° C., preferably to a temperature ranging from 50° C. to 150° C., preferably 60° C. to 150° C., preferably 70° C. to 150° C., preferably 80° C. to 150° C., and the preheated components mixed in step b) to obtain a reaction solution having a carbohydrate content ranging from 5 wt % to 50 wt % (DM carbohydrate relative to the total weight of the reaction solution) and a fructose content ranging from 40 wt % to 100 wt % (dry matter fructose relative to the DM of the carbohydrates).

In a further preferred embodiment of the present invention, the aqueous fructose-containing starting solution provided in step a) and the aqueous fructose-containing fraction that was returned are preheated before step b) to a temperature ranging from preferably 50° C. to 165° C., preferably 60° C. to 165° C., preferably 70° C. to 165° C., preferably 80° C. to 165° C., preferably to a temperature ranging from 50° C. to 160° C., preferably 60° C. to 160° C., preferably 70° C. to 160° C., preferably 80° C. to 160° C., preferably to a temperature ranging from 50° C. to 150° C., preferably 60° C. to 150° C., preferably 70° C. to 150° C., preferably 80° C. to 150° C., and the at least one homogeneous acid catalyst, preferably at least one homogeneous mineral acid catalyst, is mixed with the preheated components in step b) to obtain a reaction solution having a carbohydrate content ranging from 5 wt % to 50 wt % (DM carbohydrates relative to the total weight of the reaction solution) and a fructose content ranging from 40 wt % to 100 wt % (dry matter fructose relative to the DM of the carbohydrates).

In a preferred embodiment of the present invention, the concentration of the at least one homogeneous acidic catalyst, preferably at least one homogeneous mineral acid catalyst, ranges ranging from 0.5 wt % to 5 wt %, preferably from 0.75 wt % to 3 wt %, preferably 1 wt % to 2.5 wt % (in each case wt % relative to the total weight of the reaction solution). The concentration of the at least one homogeneous acidic catalyst, preferably at least one homogeneous mineral acid catalyst, is preferably below 5 wt %, preferably below 4 wt %, preferably below 3 wt %, preferably below 2 wt % (in each case wt % relative to the total weight of the reaction solution). The concentration of the at least one homogeneous acidic catalyst, preferably at least one homogeneous mineral acid catalyst, is preferably above 0.5 wt %, preferably above 0.75 wt %, preferably above 1 wt % (in each case wt %) in relation to the total weight of the reaction solution).

In a preferred embodiment, the at least one homogeneous acidic catalyst is a homogeneous mineral acid catalyst.

In a preferred embodiment of the present invention, the at least one homogeneous acidic catalyst is selected from hydrochloric acid (HCl), sulfuric acid ($H_2SO_4$), phosphoric acid ($H_3 PO_4$), aliphatic or aromatic carboxylic acids and aliphatic or aromatic sulfonic acids. In a preferred embodiment, the at least one homogeneous acidic catalyst is sulfuric acid ($H_2SO_4$). In a further preferred embodiment, the at least one homogeneous acidic catalyst is hydrochloric acid (HCl). In a further preferred embodiment of the present invention, the at least one acidic catalyst is phosphoric acid ($H_3PO_4$). In a further preferred embodiment, the at least one homogeneous acidic catalyst is an organic acid, in particular an aliphatic or aromatic carboxylic acid, for example oxalic acid, acetic acid or benzoic acid or an aliphatic or aromatic sulfonic acid.

In a preferred embodiment of the present invention, the carbohydrate content of the reaction solution in step b) is ranges from 5 wt % to 50 wt %, preferably 5 wt % to 45 wt %, preferably 7.5 wt % to 40 wt %, preferably 7.5 wt % to 35 wt %, preferably 10 wt % to 30 wt % (in each case the DM in relation to the total weight of reaction solution).

In a preferred embodiment, the fructose content of the reaction solution ranges from 40 wt % to 100 wt %, preferably 70 wt % to 100 wt %, preferably 80 wt % to 100 wt %, preferably 90 wt %. % to 100 wt %, preferably 95 wt % to 100 wt %, preferably 40 wt % to 99 wt %, preferably 45 wt % to 99 wt %, preferably 50 wt % to 95 wt %, preferably 45 wt % to 90 wt %, preferably 50 wt % to 85 wt % (each DM fructose relative to the dry matter of the carbohydrate portion, i.e. all the carbohydrates in the reaction solution).

In a particularly preferred embodiment, the mixing of the components used for the production of the reaction solution, i.e. in particular of the aqueous fructose-containing starting solution, and optionally the aqueous returned fructose-containing fraction and of the at least one homogeneous acidic catalyst takes place in a mixing device and/or a pipe. The mixing device and the continuous reactor system may be spatially separate assemblies interconnected by at least one pipe but may also be separate but integral components of a device.

In a preferred embodiment of the present invention, the conversion of the fructose into HMF in step c) takes place in a period of 0.1 to 20 minutes, in particular 0.1 to 15 minutes, in particular 8 to 13 minutes, in particular 4 to 10 minutes, in particular 8 to 10 minutes, preferably 0.1 to 8 minutes, preferably 0.2 to 7 minutes, preferably 0.5 to 5 minutes, preferably 1 to 4 minutes, preferably 1 to 3 minutes. The conversion of the fructose into HMF in step c) preferably takes place in a period of at most 10 min, preferably at most 9 min, preferably at most 8 min, preferably at most 7 min, preferably at most 5 min, preferably at most 4 min, preferably at most 3 min.

In a particularly preferred embodiment, the conversion in step c) is carried out at a temperature ranging from 130 to 150° C., in particular 140° C. for a period of 8 to 10 minutes, in particular 9 minutes.

In a preferred embodiment of the present invention, the conversion of the fructose to HMF in step c) takes place while adjusting a fructose conversion ranging from 1 mol % to 40 mol %, preferably 5 mol % to 35 mol %, preferably 10 mol % to 30 mol %, preferably 15 mol % to 25 mol %, preferably 20 mol % to 25 mol %. The conversion of the fructose into HMF in step c) preferably takes place subject to the adjustment of a fructose conversion of at most 40 mol %, preferably at most 35 mol %, preferably at most 30 mol %, preferably at most 25 mol %, preferably at most 20 mol %.

In a preferred embodiment of the present invention, the HMF selectivity in step c) ranges from 60 mol % to 100 mol %, preferably 65 mol % to 100 mol %, preferably 70 mol % to 100 mol %, preferably 75 mol % to 100 mol %, preferably 80 mol % to 100 mol %, preferably 85 mol % to 100 mol %, preferably 90 mol % to 100 mol %. The HMF selectivity in step c) is preferably at least 60 mol %, preferably at least 65 mol %, preferably at least 70 mol %, preferably at least 75 mol %, preferably at least 80 mol %, preferably at least 85 mol %, preferably at least 90 mol %, preferably at least 95 mol %.

In the context of the present invention, the HMF selectivity is based on the amount of fructose that is converted, with portions of other carbohydrates, in particular glucose, being disregarded.

In a particularly preferred embodiment, the continuous reactor system used in step c) is configured as a tubular reactor system. A person skilled in the art is familiar with such a continuous reactor system. In a particularly preferred embodiment, it is also possible to use a continuous reactor system, in particular a Konti system, with little backmixing. In a particularly preferred embodiment, a plug-flow reactor (PFR) may be used as the continuous reactor system. In a preferred embodiment, the continuous reactor system may also be designed as a flow tube, stirrer tank or stirrer tank cascade.

In a particularly preferred embodiment, step c) is performed at a temperature ranging from 80 to 165° C., in particular 80 to 160° C., in particular 80 to 150° C., in particular 85 to 165° C., in particular 90 to 160° C., in particular 130 to 155° C., in particular 135 to 153° C., in particular 140 to 150° C., in particular 80 to 145° C., in particular 100 to 145° C., in particular 140° C.

In a preferred embodiment of the present invention, the pressure for the conversion of the fructose present in the reaction solution to HMF in the continuous reactor system is set in step c) to avoid boiling the reaction solution. Preferably, the pressure needed in the continuous reactor system for converting the fructose present in the reaction solution to HMF ranges from 0.1 to 15 MPa.

The invention provides that a fructose conversion from 1 mol % to 40 mol % is set in step c). According to the invention, this is done at a temperature ranging from 80° C. to 165° C. It is preferably possible according to the invention to provide specifically defined fructose conversions within the parameters specified according to the invention, in particular by using the given reaction temperature, optionally in a preferred embodiment also the reaction time, for step c). On the basis of these parameters, it is also possible to set a preferred HMF selectivity according to the invention. In a manner preferred by the invention, the desired fructose conversion, and optionally the HMF selectivity, may be adjusted by removing samples during the process, analyzing sample and subsequently calculating the desired fructose conversion values to be obtained or adjusted and the optionally desired HMF selectivity.

In a preferred embodiment of the present invention, the product mixture is set to a temperature ranging from 20° C. to 80° C., preferably 25° C. to 70° C., preferably 30° C. to 60° C., preferably 30° C. to 55° C., preferably 30° C. to 50° C., preferably 30° C. to 45° C., preferably 30° C. to 40° C., preferably exactly 80° C., preferably exactly 70° C., preferably exactly 60° C., preferably exactly 55° C., preferably exactly 50° C., preferably exactly 45° C., preferably exactly 40° C., preferably exactly 35° C., preferably set exactly 30° C. in step d). Preferably, the product mixture is set to a temperature of at most 75° C., preferably at most 70° C., preferably at most 60° C., preferably at most 55° C., preferably at most 50° C., preferably at most 45° C., preferably at most 40° C., preferably set at most 35° C. in step d).

In a preferred embodiment of the present invention, the temperature of the product mixture is set in a period ranging from 0.1 to 10 minutes, preferably 0.1 to 9 minutes, preferably 0.1 to 8 minutes, preferably 0.2 to 7 min, preferably 0.2 to 6 minutes, preferably 0.5 to 5 minutes, preferably 0.5 to 4 minutes, preferably 0.5 to 3 minutes in step d). The temperature of the product mixture is preferably set in not more than 10 min, preferably not more than 9 min, preferably not more than 8 min, preferably not more than 7 min, preferably not more than 6 min, preferably not more than 5 min, preferably not more than 4 min, preferably not more than 3 min. preferably set at most 2 minutes, preferably at most 1 minute, preferably at most 0.5 minutes in step d).

In a preferred embodiment of the present invention, the product mixture obtained in step d) has a dry matter content ranging from 5 to 50 wt %. In a preferred embodiment of the present invention, the product mixture obtained in step d) has a dry matter content ranging from 5 to 70 wt %. In a preferred embodiment of the present invention, the product mixture obtained in step d) has a dry matter content of at least 5 wt %. In a preferred embodiment of the present invention, the product mixture obtained in step d) has a dry matter content of at most 70 wt %. In a preferred embodiment of the present invention, the product mixture obtained in step d) has a dry matter content of at least 10 wt %. In a preferred embodiment of the present invention, the product mixture obtained in step d) has a dry matter content of at most 60 wt %. In another preferred embodiment, the product mixture obtained in step d) before step e) is concentrated to a dry matter content ranging from 20 to 50 wt %, preferably 25 to 50 wt %, preferably 25 to 45 wt %, preferably 30 to 45 wt %, preferably 30 to 40 wt %.

In a further preferred embodiment, the product mixture obtained in step d) before step e) is concentrated to a dry matter content ranging from 10 to 70 wt %. In a further preferred embodiment, the product mixture obtained in step d) before step e) is concentrated to a dry matter content of at least 5, preferably at least 10 wt %. In a further preferred embodiment, the product mixture obtained in step d) is concentrated before step e) to a dry matter content of at most 70, preferably at most 60 wt %. In a preferred embodiment of the present invention, the product mixture obtained in step d) is adjusted to a dry matter content of 5 to 70 wt %. In a preferred embodiment of the present invention, the product mixture obtained in step d) is adjusted to a dry matter content of at least 5 wt %. In a preferred embodiment of the present invention, the product mixture obtained in step d) is adjusted to a dry matter content of at most 70 wt %. In a preferred embodiment of the present invention, the product mixture obtained in step d) is adjusted to a dry matter content of at least 10 wt %. In a preferred embodiment of the present invention, the product mixture obtained in step d) is adjusted to a dry matter content of at most 60 wt %.

Before step e), the product mixture obtained in step d) is preferably adjusted to a water content of 50 to 80 wt %, preferably 50 to 75 wt %, preferably 55 to 75 wt %, preferably 55 to 70 wt. %, preferably 60 to 70 wt % before step e).

Before step e), the product mixture obtained in step d) is preferably adjusted to a water content ranging from 30 to 95 wt %.

Before step e), the product mixture obtained in step d) is preferably adjusted to a liquid content ranging from 30 to 95 wt %.

In a preferred embodiment of the present invention, the product mixture provided to step e) has a dry matter content ranging from 5 to 70 wt %. In a preferred embodiment of the present invention, the product mixture provided to step e) has a dry matter content ranging from 10 to 60 wt %. In a preferred embodiment of the present invention, the product mixture provided to step e) has a dry matter content ranging from 15 to 55 wt %.

In a preferred embodiment of the present invention, the chromatography is a chromatography on ion exchange resins, in particular on cation exchange resins.

In a particularly preferred embodiment of the present invention, the chromatography, in particular the chromatography on ion exchange resins, in particular the chromatography on cation exchange resins, is an ion exchange chromatography, in particular a cation exchange chromatography.

The purification of the product mixture obtained in step d) is preferably carried out continuously by using a chromatography according to step e). Continuous chromatography is also preferably understood to refer to a simulated countercurrent chromatography such as Simulated Moving Bed Chromatography (SMB).

Continuous chromatography methods are well known to a person skilled in the art. For example, US 2011/0137084 A1 shows the mode of operation of the SMB method. Other suitable chromatography methods are described in A. Rajendran et al.; J. Chromatogr. A 1216 (2009), pages 709-738.

Simulated Moving Bed (SMB) systems or enhancements of the SMB system, such as Sequential SMB (SSMB), Intermittent/Improved SMB (ISMB) or New MCI (NMCI) advantageously allow for the separation and recovery of the four fractions described in continuous operation.

In a preferred embodiment of the present invention, the chromatography, in particular the chromatography on ion exchange resins, in step e) is a Simulated Moving Bed (SMB) method, a Sequentially Simulated Moving Bed (SSMB) method, or an Improved Simulated Moving Bed method or an (Intermittent) Simulated Moving Bed method (ISMB). Preferably, the chromatography, in particular the chromatography on ion exchange resins, in step e) is a Simulated Moving Bed method (SMB), a Sequential Simulated Moving Bed method (SSMB), an Improved Simulated Moving Bed method (ISMB) or a New MCI Procedure (NMCI). By using a Simulated Moving Bed (SMB) method, a Sequentially Simulated Moving Bed (SSMB) method, an Improved Simulated Moving Bed (ISMB) method, or a New MCI (NMCI) method in step e), it is advantageously possible to carry out the purification of the product mixture obtained in step d) for the separation of an HMF fraction, a carbohydrate/acid fraction, a fructose fraction and a levulinic and formic acid fraction in a continuous procedure.

In a preferred embodiment of the present invention, the chromatography in step e), in particular chromatography on ion exchange resins, in particular on cation exchange resins, is a one-step process. The chromatography, in particular chromatography on ion exchange resins, in particular on cation exchange resins, in step e) is preferably a multi-stage process, preferably a two-stage process.

The chromatography, in particular the chromatography on ion exchange resins, in particular the chromatography on cation exchange resins, in step e) preferably comprises a plurality of stages, preferably at least two stages, preferably at least three stages, preferably exactly two stages, preferably exactly three stages.

In a preferred embodiment of the present invention, a separation of at least one fraction, preferably exactly one fraction, in particular an HMF fraction or a carbohydrate/acid fraction, preferably of at least two fractions, prefers exactly two fractions, preferably exactly three fractions occurs in step e) in a first step of the chromatography.

In a further preferred embodiment of the present invention, a separation of at least one fraction, preferably exactly one fraction, preferably at least two fractions, preferably exactly two fractions, preferably exactly three fractions, especially one Carbohydrate/acid fraction, a fructose fraction and a levulinic and formic acid fraction or an HMF fraction, a fructose fraction and a levulinic and formic acid fraction occurs in step e) in a second stage of the chromatography.

In a preferred embodiment of the present invention, the first step of the chromatography in step e) is a chromatography method selected from the group consisting of the Simulated Moving Bed (SMB) method, the Sequentially Simulated Moving Bed (SSMB) method, the Improved Simulated Moving Bed (ISMB) method and the New MCI Method (NMCI).

Preferably, the first step of the chromatography in step e) is an Improved Simulated Moving Bed (ISMB) method. Preferably, in a first stage of step c), a separation of at least one fraction, preferably exactly one fraction, in particular an HMF fraction or a carbohydrate/acid fraction occurs, said fractions being selected by means of a chromatography method from the group consisting of the Simulated Moving Bed (SMB) method, the Sequentially Simulated Moving Bed (SSMB) method, the Improved Simulated Moving Bed (ISMB) method and the New MCI (NMCI) method, preferably by means of an Improved Simulated Moving Bed (ISMB) method.

In a preferred embodiment of the present invention, the second step of the chromatography in step e) is a chromatography method selected from the group consisting of the Simulated Moving Bed (SMB) method, the Sequentially Simulated Moving Bed (SSMB) method, the Improved Simulated Moving Bed Method (ISMB) method and the New MCI Method (NMCI) method.

Preferably, the first step of the chromatography in step e) is a New MCI method (NMCI). Preference is given in step e) in a second stage to the separation of at least one fraction, preferably exactly one fraction, preferably at least two fractions, preferably exactly two fractions, preferably at least three fractions, preferably exactly three fractions, in particular a carbohydrate/acid fraction, a fructose fraction and a levulinic and formic acid fraction or an HMF fraction, a fructose fraction and a levulinic and formic acid fraction, by means of a chromatography method selected from the group consisting of the Simulated Moving Bed (SMB) method, the sequential Simulated Moving Bed (SSMB), the Improved Simulated Moving Bed (ISMB) method, and the New MCI (NMCI) method, preferably by means of a New MCI (NMCI) method.

In particular, an at least two-stage chromatography separation is preferred, in which the HMF fraction is separated in the first stage. Alternatively, the carbohydrate/acid fraction can be separated in the first stage as well. The first stage of the at least two-stage chromatography separation is preferably a Moving Bed method (ISMB). Preferably, the second stage of at least two-step chromatography separation is a New MCI method (NMCI).

In particular, a two-stage chromatography separation is preferred, in which the HMF fraction is separated in the first stage. Alternatively, the carbohydrate/acid fraction can be separated in the first stage as well. Preferably, the first stage of the two-stage chromatography separation is a Moving Bed method (ISMB). Preferably, the second stage of the two-stage chromatography separation is a New MCI method (NMCI). Preferably, the levulinic and formic acid fractions, the fructose fraction and the carbohydrate/acid fraction are separated from one another in the second stage of the two-stage chromatography separation. Alternatively, the levulinic and formic acid fractions, the fructose fraction and the HMF fraction are separated from each other in the second stage of the two-stage chromatography separation. In a preferred embodiment of the present invention, the chromatography, in particular the chromatography on ion exchange resins in step e) is a chromatography on cation exchange resins.

In a preferred embodiment of the present invention, the chromatography, in particular the chromatography on ion exchange resins in step e) is carried out using a cation exchange resin in the H$^+$ form.

In a further preferred embodiment, the chromatography, in particular the chromatography on ion exchange resins, in particular the chromatography on cation exchange resins, has an upstream filtration of the product mixture, preferably by means of a suitable filter or a suitable filter system, and a decolorization and/or purification of the product mixture, preferably a decolorization and/or purification over activated carbon. A filtration of the product mixture preferably takes place after step d) by means of a suitable filter or a suitable filter system and decolorization and/or purification of the product mixture, for example via activated carbon. A filtration of the product mixture preferably takes place before step e) by means of a suitable filter or a suitable filter system and decolorization and/or purification of the product mixture, for example via activated carbon. In a particularly preferred embodiment a filtration by means of a suitable filter or a suitable filter system, a decolorization and/or purification of the product mixture, in particular via activated carbon, a concentration and, if appropriate, repeated filtration by means of a suitable filter or a suitable filter system are performed after process step c), in particular after process step d) and before step e) in any order. In a particularly preferred embodiment, a filtration by means of a suitable filter or a suitable filter system if performed first, and then a decolorization and/or purification, in particular via activated carbon, followed by a concentration and optionally a re-filtration by means of a suitable filter or a suitable filter system are performed in this order after step c), in particular after step d), and before step e).

Preferably, the filtration removes from the product mixture any unwanted byproducts, in particular soluble and insoluble humic substances, by filtering the product mixture through a suitable filter or a suitable filter system and decolorizing and/or purifying it via, for example, activated carbon. The life of the material used for the chromatography, in particular the chromatography on ion exchange resins, in particular the chromatography on cation exchange resins, in particular resin, is preferably prolonged by the removal of undesired byproducts, in particular soluble and insoluble humic substances.

In a preferred embodiment, the chromatography, in particular the chromatography on ion exchange resins, is performed in step e) at a temperature ranging from 40° C. to 80° C., preferably 40° C. to 70° C., preferably 40° C. to 60° C., preferably 50° C. to 80° C., preferably 50° C. to 70° C., preferably 50° C. to 60° C., preferably 60° C. to 80° C., preferably 60° C. to 70° C.

The fructose fraction separated in step e), preferably obtained in a step f), is preferably continuously returned to process step a). In this case, the fructose fraction separated in step e), preferably obtained in a step f), is advantageously largely, preferably completely, free from the levulinic acid that is created. In a further preferred embodiment, the fructose fraction separated in step e), preferably obtained in a step f), is advantageously largely, preferably completely, free from the levulinic and formic acid that is created.

In a particularly preferred embodiment, the entire fructose fraction separated in step e), preferably obtained in a step f), is returned continuously, if appropriate after concentration, to step a). In a further preferred embodiment, the fructose fraction separated in step e), preferably obtained in a step f), is continuously, if appropriate after concentration, least partially, in particular at least 70%, preferably at least 80%, preferably at least 90%, preferably at least 95%, preferably at least 98%, preferably at least 99%, returned to step a) (in each case wt % of the returned fructose fraction relative to the fructose fraction separated in step e), preferably obtained in a step f).

In a particularly preferred embodiment, the ratio of fructose to glucose in the returned fructose fraction is not less than in the aqueous fructose-containing starting solution provided in step a).

In a further preferred embodiment of the present invention, the carbohydrate/acid fraction separated in step e), preferably obtained in a step f), has a sufficiently high purity, is, in particular, free from fermentation inhibitors, so that it can be used directly, if appropriate after concentration, both as feed in fermentative processes, in particular for the production of ethanol, in particular fermentation of ethanol, and as starting material in chemical processes, in particular the oxidation of glucose to gluconic acid.

In a further preferred embodiment, the carbohydrate/acid fraction separated in step e), preferably obtained in a step f), is used for the production of ethanol, in particular for fermentation of ethanol, in particular for the production of bioethanol gluconic acid.

The present invention therefore also provides a process for the production of a feed for fermentative processes, in particular for the production of ethanol, in particular fermentation of ethanol, or for the production of a starting material, i.e. the starting material in chemical processes, in particular for the production of gluconic acid, within the scope of which a method of the present invention with the process steps a) to e), preferably a) to f), is performed to obtain a carbohydrate/acid fraction, which can be used as feed or starting material.

In a preferred embodiment of the present invention, the carbohydrate/acid fraction separated in step e), preferably obtained in a step f), is used for the production of ethanol, in particular for fermentation of ethanol, and in particular for the production of bioethanol.

In a particularly preferred embodiment, a method is provided for the production of ethanol, in particular the fermentation of ethanol, within the scope of which the method according to the invention, in particular process steps a) to e), preferably a) to f), is performed in particular for obtaining a carbohydrate/acid fraction, wherein the carbohydrate/acid fraction is used for the production of ethanol, in particular fermentation of ethanol, in particular for the extraction of bioethanol.

In a further preferred embodiment, in the case of the use of sulfuric acid as the homogeneous acidic catalyst, preferably the mineral acid catalyst, the sulfuric acid is separated in step e) of the method according to the invention as a sulfuric acid fraction and the sulfuric acid fraction obtained is used in step f) for the production of ethanol, in particular the fermentation of ethanol, in particular for the production of bioethanol.

In a further preferred embodiment, the carbohydrate/acid fraction separated in step e), preferably obtained in a step f), is used for the production gluconic acid, optionally after concentration.

In a particularly preferred embodiment, a method for the production of gluconic acid is provided which comprises the method according to the invention, in particular process steps a) to e), preferably a) to f), which can be used in particular to obtain a carbohydrate/acid fraction which is suitable for the production of glucose and a subsequent oxidation of the glucose to gluconic acid.

In a preferred embodiment of the present invention, the levulinic and formic acid fraction separated in step e) and preferably obtained in step f) is used for the isolation of levulinic and formic acid. In a further preferred embodiment, the levulinic and formic acid fraction obtained in step e), preferably obtained in a step f), is used to isolate levulinic acid. In a further preferred embodiment, the levulinic and formic acid fraction separated in step e) and preferably obtained in step f) is used for the isolation of formic acid.

The present invention therefore also relates to a method for the production of levulinic acid, formic acid or levulinic acid and formic acid, with a method comprising the steps a) to e), preferably a) to f), of the present invention being performed and levulinic acid, formic acid or levulinic acid and formic acid being obtained in a step f).

In a further preferred embodiment of the present invention, the HMF fraction obtained in step e), preferably obtained in step f), is oxidized to 2.5 furandicarboxylic acid (FDCA) directly, optionally after concentration, that is to say without the need for further purification, in an additional step.

The present invention therefore also relates to a method for the production of FDCA comprising steps a) to e), preferably a) to f), of the present invention, wherein the HMF fraction separated in step e), preferably obtained in a step f), is oxidized preferably directly, optionally after concentration, and to FDCA without the need for extensive further purification.

According to the invention, the carbohydrate/acid fraction separated in step e), preferably obtained in a step f), comprises at least 20 wt % of the glucose present in the product mixture (in each case relative to the product mixture).

According to the invention, the carbohydrate/acid fraction contains 0.8 wt % to 100 wt % of glucose, 0 wt % to 99.2 wt % fructose, at most 2 wt %, preferably at most 1 wt %, preferably at most 0.5 wt %, preferably at most 0.1 wt % levulinic and formic acid and at most 10 wt %, preferably at most 5 wt %, preferably at most 2 wt %, more preferably at most 1 wt %, preferably at most 0.5 wt %, preferably at most 0.1 wt % HMF (in each case DM, based on the sum of the analyzed components (glucose, fructose, levulinic acid, formic acid, HMF, difructose anhydride (DFA))). According to the invention, the carbohydrate/acid fraction preferably contains at most 10 wt %, more preferably at most 5 wt % of HMF.

The fructose fraction separated in step e), preferably obtained in a step f), contains at least 70 wt %, preferably at least 80 wt % of the fructose contained in the product mixture (in each case relative to the product mixture).

According to the invention, the fructose fraction contains 0 wt % to 60 wt % glucose, 40 wt % to 100 wt % fructose, at most 2 wt %, preferably at most 1 wt %, preferably at most 0.5 wt %, preferably at most 0.1 wt % levulinic acid, at most 2 wt %, preferably at most 1.5 wt %, preferably at most 1 wt %, preferably at most 0.5 wt. %, preferably at most 0.25 wt %, preferably at most 0.1 wt % formic acid and at most 2 wt %, preferably at most 1.5 wt %, preferably at most 1 wt %, preferably at most 0.8 wt %, preferably at most 0.6 wt %, preferably at most 0.4 wt %, preferably at most 0.2 wt %, preferably at most 0.1 wt % HMF (each DM, based on the sum of the analyzed components (glucose, fructose, levulinic acid, formic acid, HMF, difructose anhydride (DFA)). According to the invention, the fructose fraction preferably contains at most 2 wt % HMF. According to the invention, the fructose fraction preferably contains at most 2 wt % levulinic acid. In a particularly preferred embodiment, the ratio of fructose to glucose in the fructose fraction is not less than in the aqueous fructose-containing starting solution provided in step a).

According to the invention, the levulinic and formic acid fraction separated in step e), preferably obtained in a step f), contains at least 60 wt %, preferably at least 65 wt %, preferably at least 70 wt %, preferably at least 80 wt %, preferably at least 90 wt %, preferably at least 95 wt %, preferably at least 98 wt %, preferably at least 99 wt %, preferably at least 99.5 wt %, preferably at least 99.8 wt %, preferably 100 wt % of the levulinic and formic acids contained in the product mixture (in each case DM, relative to the product mixture).

According to the invention, the levulinic and formic acid fractions contain from 50 wt % to 100 wt %, preferably from 60 wt % to 100 wt %, more preferably from 65 wt % to 100 wt %, preferably from 70 wt % to 100 wt %, preferably from 80 wt % to 100 wt %, preferably from 90 wt % to 100 wt %, preferably from 95 wt % to 100 wt %, preferably 98% to 100%, preferably 99% to 100%, preferably 99.5% to 100%, preferably 99.7 wt % to 100 wt % of levulinic and formic acid (in each case DM, relative to the sum of the components analyzed (glucose, fructose, levulinic acid, formic acid, HMF, difructose anhydride (DFA))). Preferably, according to the invention, the levulinic and formic acid fractions contain at least 50 wt % of levulinic acid, more preferably at least 60 wt % levulinic acid, more preferably at least 70 wt % levulinic acid.

The HMF fraction obtained in step e), preferably obtained in a step f), contains at least 70 wt %, preferably at least 80 wt %, more preferably at least 90 wt %, preferably at least 98 wt %. %, preferably at least 99 wt %, preferably at least 99.5 wt %, preferably at least 99.8 wt %, preferably 100 wt % of the HMF contained in the product mixture (in each case TS, based on product mixture), According to the invention, the HMF fraction contains 80 wt % to 100 wt %, preferably 85 wt % to 100 wt %, preferably 90 wt % to 100 wt %, preferably 95 wt % to 100 wt. %, preferably 98 wt. % to 100 wt. %, preferably 99 wt. % to 100 wt. %, preferably 99.5 wt. % to 100 wt. %, preferably 99, 7 wt % to 100 wt % HMF and at most 16 wt %, preferably at most 14 wt %, preferably at most 12 wt %, preferably at most 10 wt %, preferably at most 8 wt %, preferably at most 6 wt %, preferably at most 4 wt %, preferably at most 2 wt %, preferably at most 1 wt % levulinic and formic acid, at most 2 wt %, preferably at most 1 wt %, preferably at most 0.8 wt %, preferably at most 0.6 wt %, preferably at most 0.4 wt %, preferably at most 0.2 wt %, preferably at most 0.1 wt % glucose and at most 2 wt %, preferably at most 1 wt %, preferably at most 0.8 wt %, preferably at most 0.6 wt %, preferably highest ns 0.4 wt %, preferably at most 0.2 wt %, preferably at most 0.1 wt % fructose (in each case DM, based on the sum of the components analyzed (glucose, fructose, levulinic acid, formic acid, HMF difructose anhydride (DFA))).

In a preferred embodiment, no organic solvents are used in the process according to the invention, in particular during steps a) to e), preferably a) to f).

In a preferred embodiment, the method according to the invention, in particular during steps a) to e), preferably a) to f), is not carried out under oxygen-reduced conditions.

In a preferred embodiment, the reaction solution is not brought to a temperature ranging from 80 to 165° C. by steam injection.

In the context of the present invention, a plug-flow reactor (PFR) is understood to be a so-called ideal flow tube (IT), that is to say a tubular reactor in which there is a drop flow. Such a reactor is, in particular, also distinguished by the fact that no mixing, backflow or turbulence of the reaction solution takes place, but rather that there is a uniform flow takes with a mass conversion taking place at the same time. The plug-flow reactor ensures, in particular, that each substance fed into the plug-flow reactor, in particular each component that fed in, is continuously reacted under the same conditions, i.e. all components are exposed to the conversion process for the same period of time.

According to the invention, an "aqueous recirculated fructose-containing fraction" is understood to be an aqueous fraction of unreacted fructose obtained from the chromatography carried out according to the method of the invention, in particular the chromatography on ion exchange resins, in particular the chromatography on cation exchange resins, which is largely, preferably completely free from byproducts created during the fructose conversion, especially levulinic and formic acid and humic substances. In this case, the resulting aqueous fraction of unreacted fructose has such a high purity that it is returned in a preferred embodiment directly, optionally after concentration, i.e. without further purification, to the process step a) and, after having been mixed with the aqueous fructose-containing starting solution and the at least one homogeneous acidic catalyst, is then available for a further conversion to HMF. Since, in this preferred embodiment, initially no aqueous returned fructose-containing fraction is available during the initiation of the method according to the invention, a correspondingly larger amount of aqueous fructose-containing starting solution is preferably used in this case instead.

In connection with the present invention, "adjustment of a fructose conversion" means that the reaction parameters used for the conversion of fructose to HMF, in particular the reaction temperature and the reaction time in the reactor, are chosen so that there is only a limited conversion of the fructose of a maximum of 40 mol %, by means of which a high HMF selectivity and thus a low byproduct creation can be achieved.

The term "and/or" in the context of the present invention is understood to mean that all members of a group which are connected by the term "and/or" are disclosed both alternatively to each other and in each case cumulatively in any combination. This means for the expression "A, B and/or C" that the following disclosure content is to be understood: A or B or C or (A and B) or (A and C) or (B and C) or (A and B and C).

In the context of the present invention, the term "comprising" is understood to mean that, in addition to the elements explicitly covered by the term, further elements not explicitly mentioned may also be added. In the context of the present invention, this term also means that only the explicitly mentioned elements are included and no further elements are present. In this particular embodiment, the meaning of the term "comprising" is synonymous with the term "consisting of". In addition, the term "comprehensive" also encompasses entities which, in addition to the explicitly mentioned elements, contain other elements which are not mentioned as well, but which are of a functionally and qualitatively subordinate nature. In this embodiment, the term "comprising" is synonymous with the term "consisting substantially of".

Further preferred embodiments are described in the subclaims.

The present invention will be illustrated by the following example and associated figures.

Figure 11:
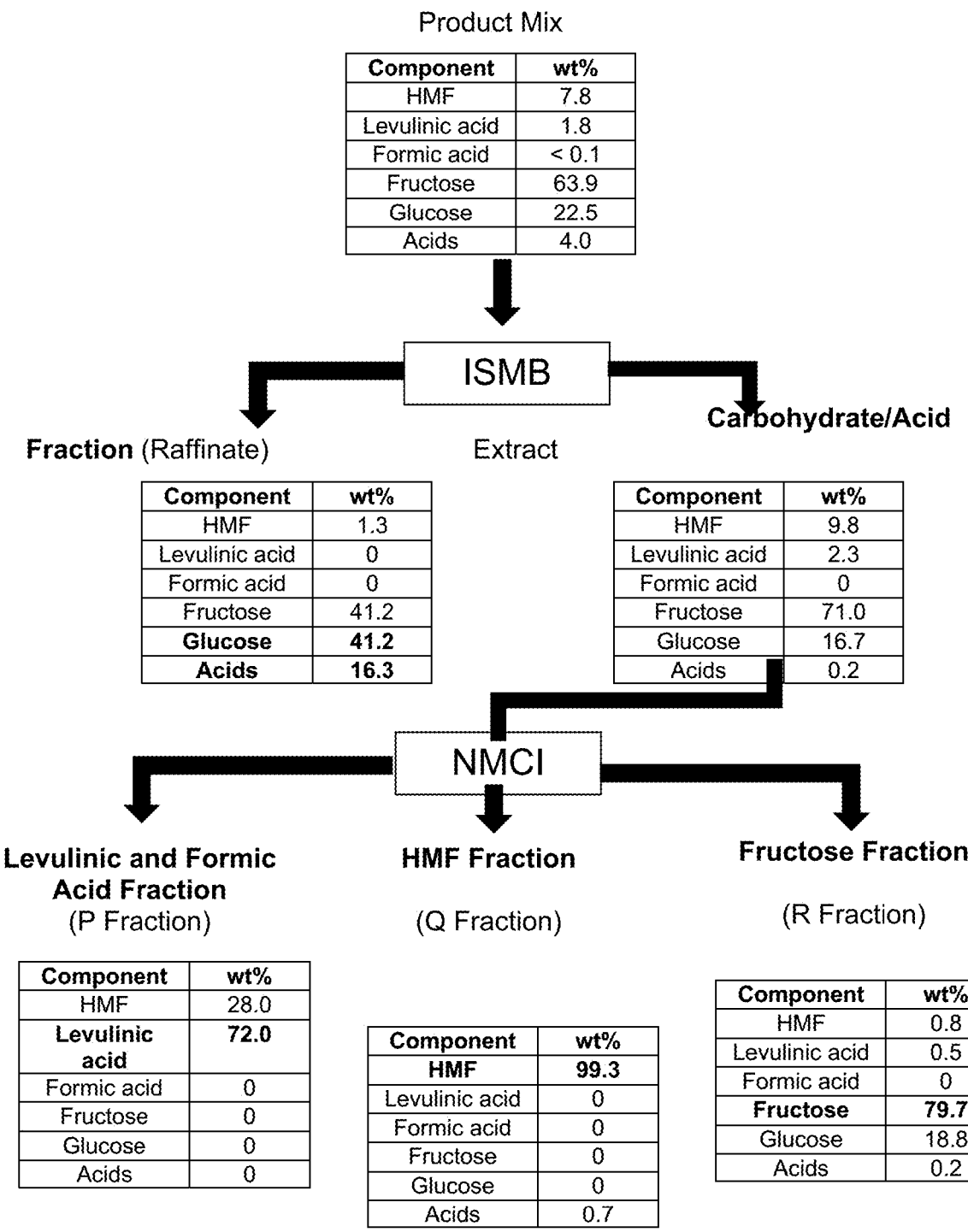

FIG. 11 schematically shows the performance of a two-stage chromatographic separation of an HMF-containing product mixture with a low dry matter content into a carbohydrate/acid fraction (raffinate), a levulinic and formic acid fraction (P fraction), an HMF fraction (Q fraction) and a fructose fraction (R fraction). ISMB=Improved Simulated Moving Bed, NMCI=New MCI.

Figure 12:
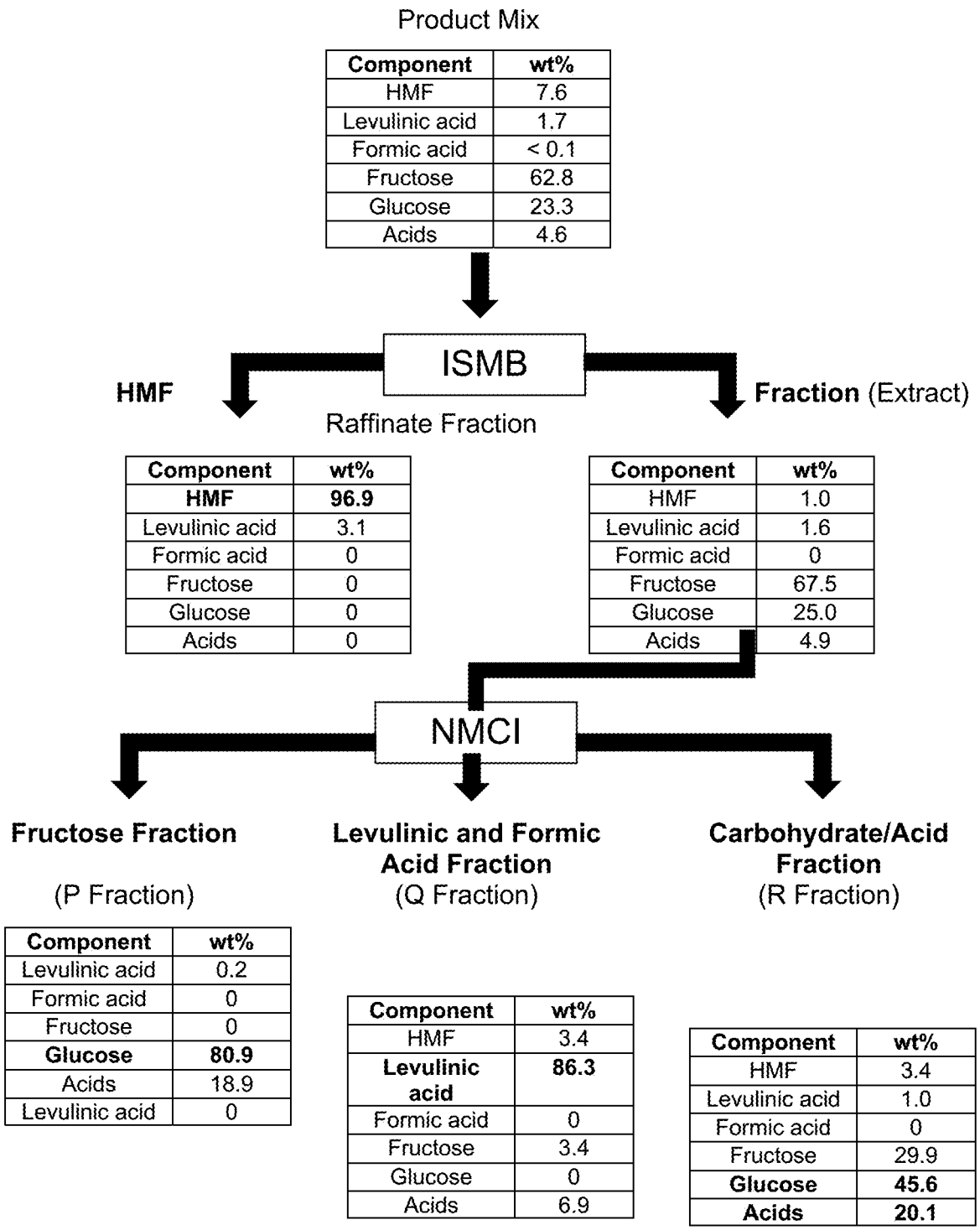

FIG. 12 shows schematically the performance of a two-stage chromatographic separation of an HMF-containing product mixture with high dry matter content in an HMF fraction (extract), a fructose fraction (P fraction), a levulinic and formic acid fraction (Q fraction) and a carbohydrate/acid fraction (R fraction). ISMB=Improved Simulated Moving Bed, NMCI=New MCI.

Figure 13:
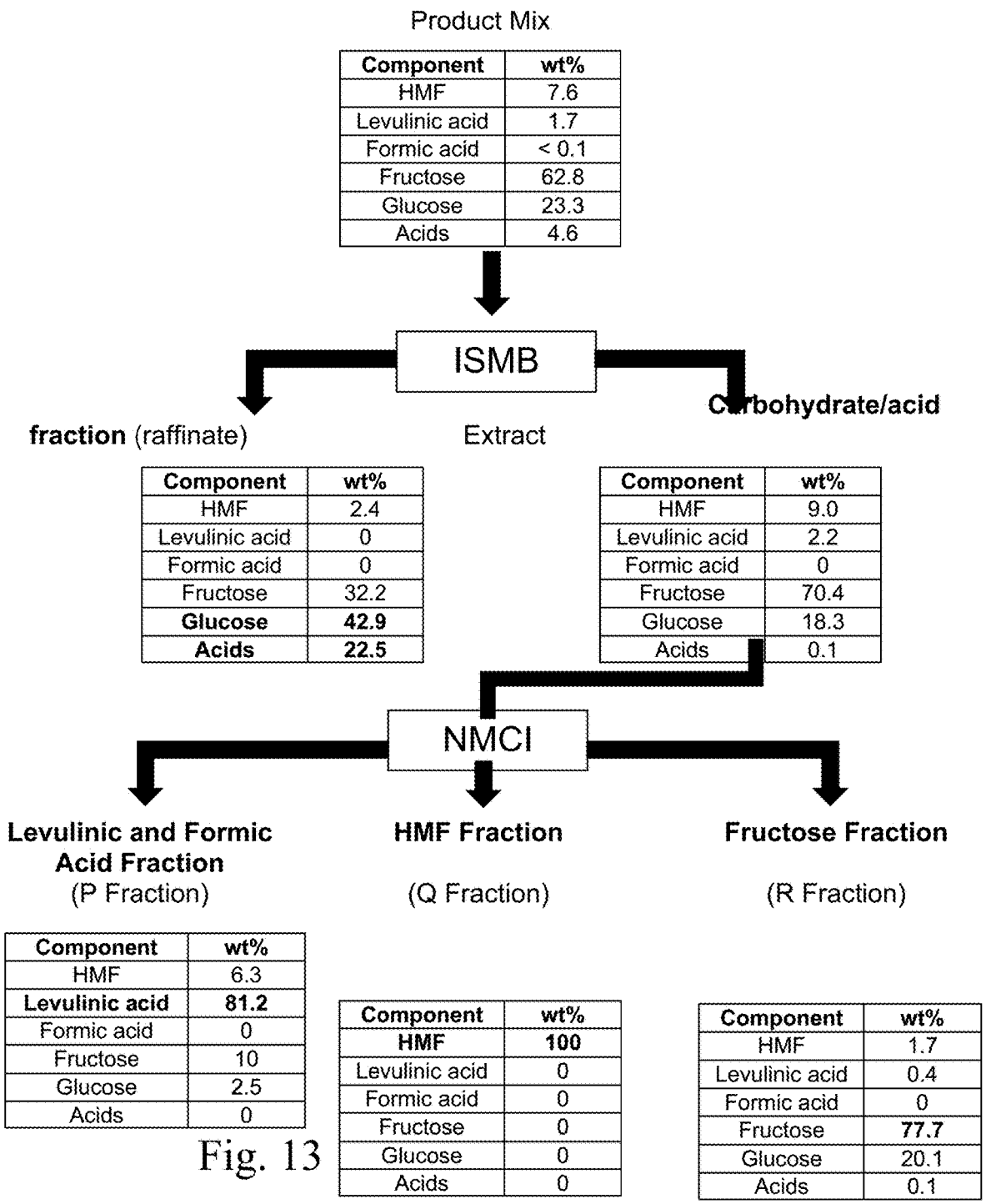

FIG. 13 schematically shows the performance of a two-stage chromatographic separation of an HMF-containing product mixture with a high dry matter content into a carbohydrate/acid fraction (raffinate), a levulinic and formic acid fraction (P fraction), an HMF fraction (Q fraction) and a fructose fraction (R fraction). ISMB=Improved Simulated Moving Bed, NMCI=New MCI.

EXAMPLES

Figure 2:
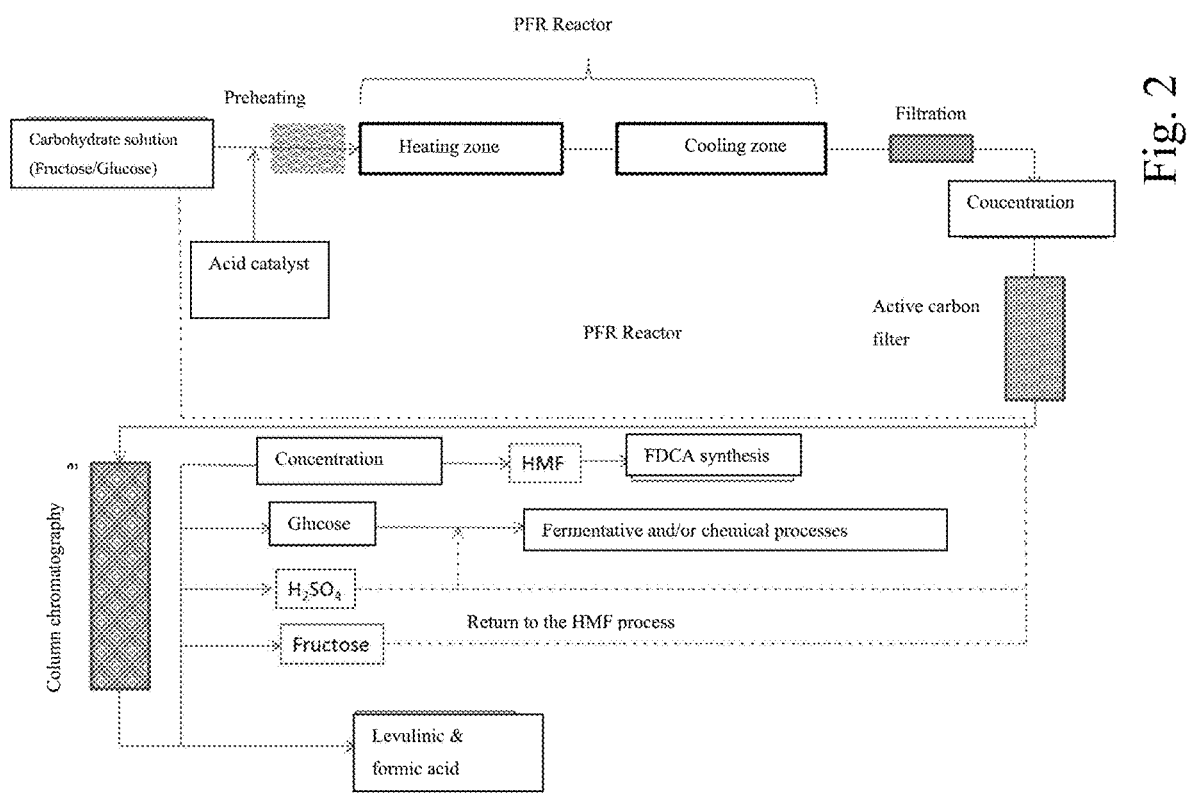
FIG. 2 shows a process diagram of the method according to the invention in which the components are heated together after they have been mixed.
Figure 3:
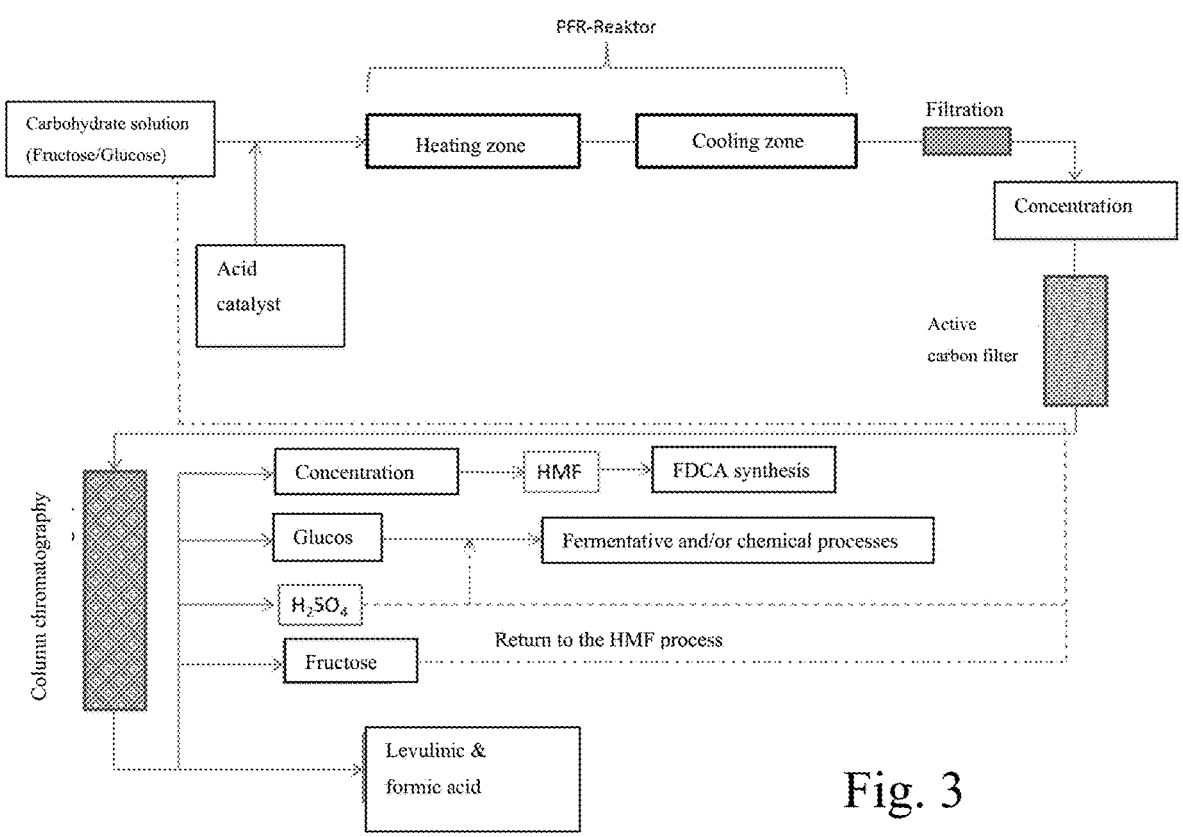
FIG. 3 shows a process diagram of the method according to the invention in which the carbohydrate solution and the acidic catalyst are mixed upstream of the reactor without first being preheated.

A) General Experimental Setup According to FIG. 2

The reaction solution used is a carbohydrate solution with a variable fructose/glucose ratio in 0.5-1.0 wt % of sulfuric acid. The carbohydrate content is 15% to 25% dry matter (DM, based on the total weight of the reaction solution).

Figure 1:
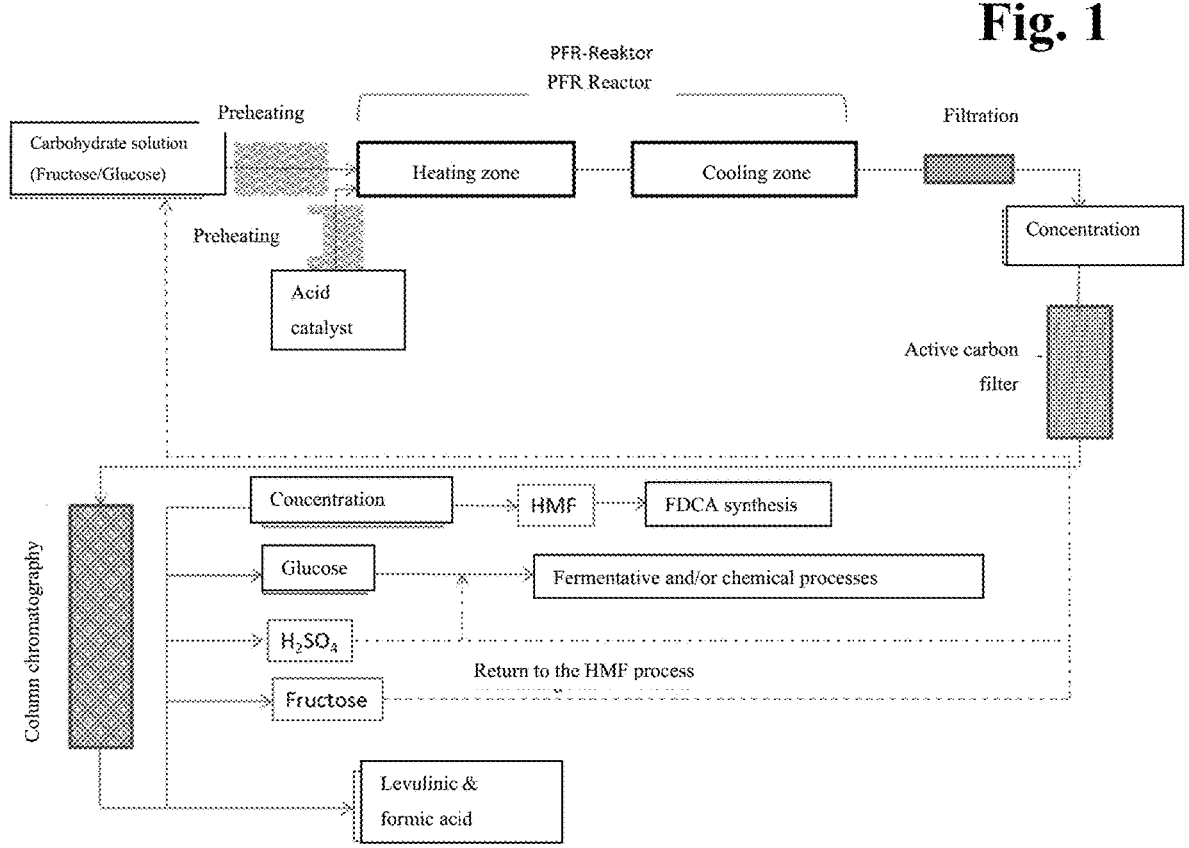
FIG. 1 shows a process diagram of the method according to the invention in which the carbohydrate solution and the acidic catalyst are preheated separately before the components are mixed.

Using a HPLC pump, the reaction solution first passes through a double tube heat exchanger (internal diameter 3 mm, length 1614 mm, volume 11.4 ml) and then pumped into the continuously operated tubular reactor (internal diameter 6 mm, length 630 mm, volume 17.8 ml) (FIG. 2, alternative embodiment with separate preheating according to FIG. 1). The temperature of the double tube heat exchanger is controlled with thermostats as the heating medium, which are operated with ethylene glycol. The temperature of the actual reactor is controlled by means of an electric heater in the form of a heating hose. The temperature sensor used to regulate the heating hose is located approximately halfway inside the heating hose. Control measurements showed that, in the residence time range used, there is a maximum temperature difference between the temperature sensor in the heating hose and the temperature of the reaction solution on the reactor (measured in the reaction solution in the center of the hose). In each case, the control temperature of the heating hose is provided. There is a direct transition from the heating zone of the reactor to the cooling zone (double tube heat exchanger with internal diameter of 6 mm, length 400 mm, volume 11.3 ml). In the cooling zone, the product mixture is cooled from the reaction temperature to approximately 50° C., and then the solution is filtered through a sintered filter (7 μm pore size) and collected. The pressure in the reaction system is adjusted by means of a pressure retention valve so that the reaction solution does not boil (and therefore does not outgas) (approx. 0.5-0.6 MPa at a reaction temperature of 150° C.).

Figure 4:
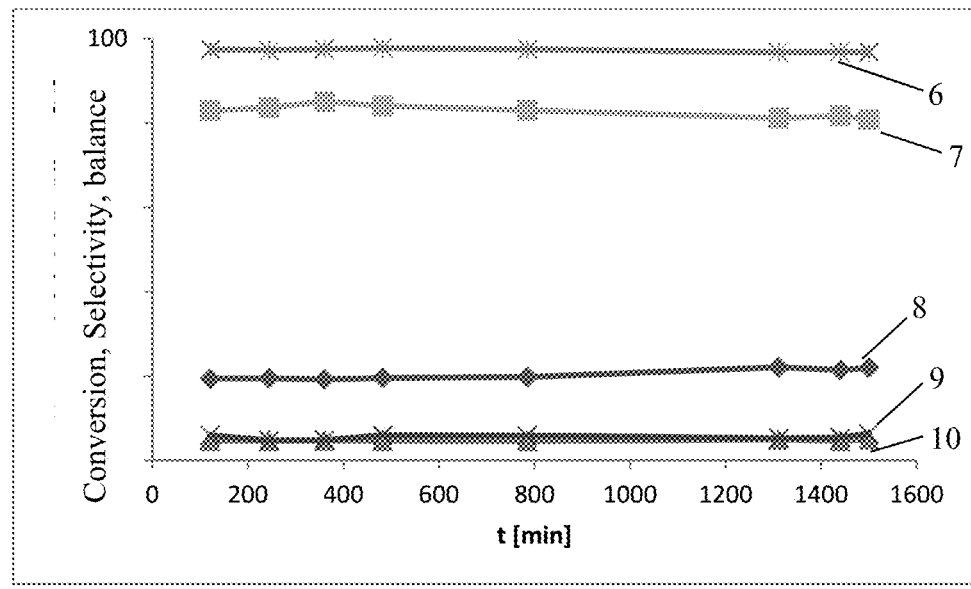
FIG. 4 shows the course of the reaction in Example 1, with 18.5 wt % carbohydrate solution returned from the chromatography, 0.75 wt % sulfuric acid, 150° C., with a residence time, i.e. a reaction time according to process step c)) of 6 min and with the carbon balance (6), HMF selectivity (7), fructose conversion (8), formic acid (9), levulinic acid (10).

B) Example 1: HMF Synthesis with a Chromatographically Returned Fructose Solution (18.5 wt %) at 150° C. in 0.75% Acid A 18.5 wt % carbohydrate solution (according to A, above) (86.1% fructose, 13.8% glucose, 0.75 wt % sulfuric acid), in which 100% of the carbohydrate portion consists of a fructose fraction returned from the chromatographic separation process, is first preheated to 80° C. and then continuously converted in step c) at a temperature of 150° C. with a residence time (relative to the heating zone) of 6 min over a test period of 25 h. Over the course of the reaction, samples were taken regularly and the composition was analyzed by means of HPLC. FIG. 4 shows the results obtained with respect to the fructose conversion, the selectivities and the carbon balance (carbon balance=(Σ[unreacted sugars, HMF and formic acid (in mol)] *100/used sugar (in moles))). Glucose was not significantly converted under the chosen reaction conditions, which is why the selectivities refer to the converted fructose.

The composition of the product mixture was constant over the entire experimental period. The fructose conversion (8) was approx. 20%, the HMF selectivity (7) approx. 83% and the carbon balance (6) 97%. The 3% missing in the carbon balance consisted of analytically unrecognized intermediates and byproducts, such as, for example, soluble and insoluble humic substances.

Figure 5:
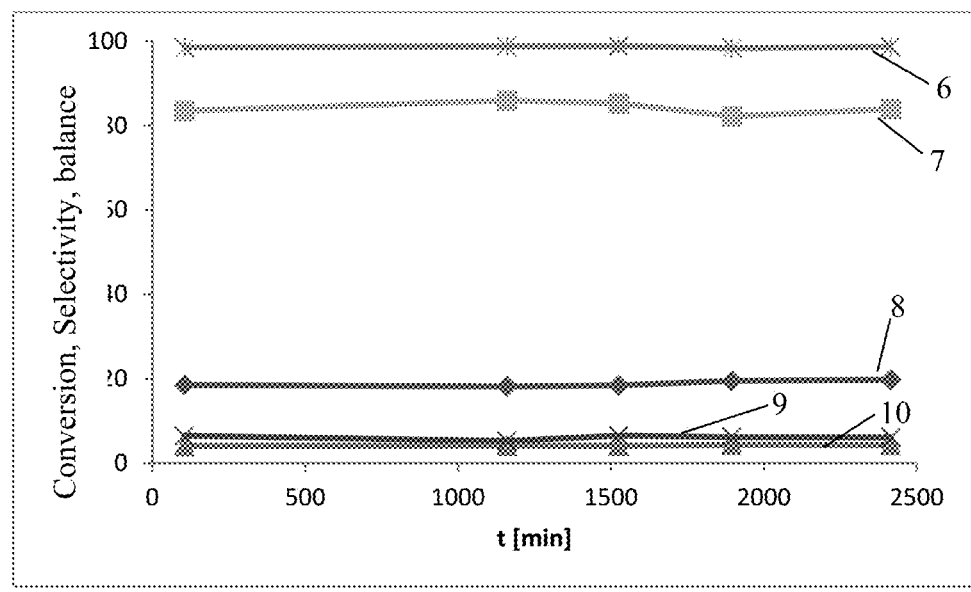
FIG. 5 shows the course of the reaction in Example 2, with 20 wt % carbohydrate, 0.75 wt % sulfuric acid, 150° C., with a residence time of 6 min and with the carbon balance (6), HMF selectivity (7), fructose turnover (8), formic acid (9), levulinic acid (10).

Example 2: HMF Synthesis with 20% Carbohydrate Solution at 150° C. with 0.75% Acid A 20 wt % fructose solution (according to A, above) (80% fructose, 20% glucose) in 0.75 wt % sulfuric acid was preheated first to a temperature of 80° C. and then in step c) continuously converted at a temperature of 150° C. with a residence time (relative to the heating zone) of 6 min over a test period of 40 h. Over the course of the reaction, samples were taken regularly and the composition was analyzed by means of HPLC. FIG. 5 shows the results obtained with respect to fructose conversion, selectivities and carbon balance.

Throughout the experiment, the composition of the product mixture was constant. The fructose conversion (8) was approximately 19%, the HMF selectivity (7) approximately 84% and the carbon balance (6) 98.6%. The 1.4% missing in the carbon balance consisted of analytically unrecognized intermediates and byproducts, such as, for example, soluble and insoluble humic substances.

Figure 6:
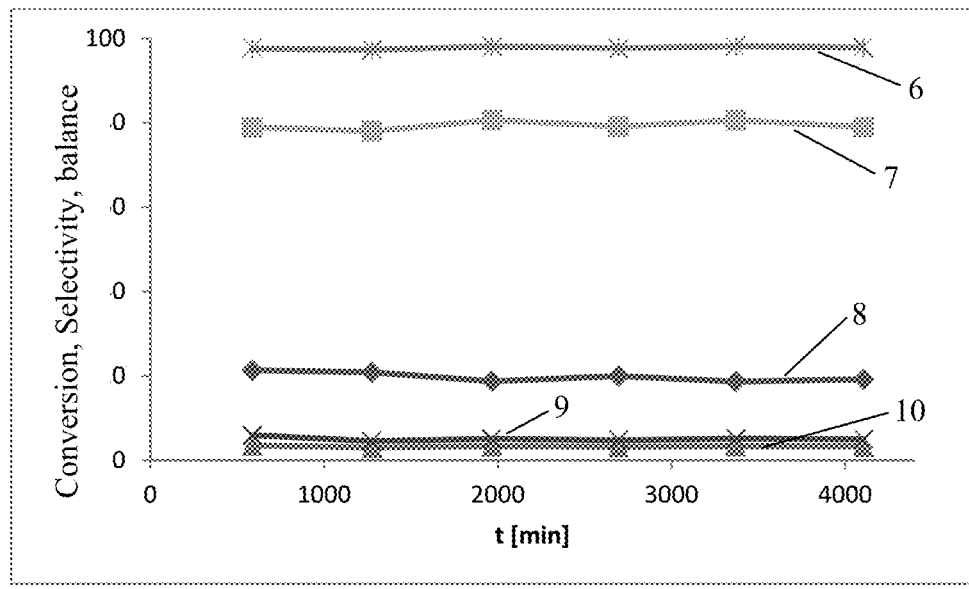
FIG. 6 shows the course of the reaction in Example 3 with 15 wt % carbohydrate, 0.5 wt % sulfuric acid, 153° C., with a residence time of 7 min and with the carbon balance (6), HMF selectivity (7), fructose turnover (8), formic acid (9), levulinic acid (10).

Example 3: HMF Synthesis with 15% Carbohydrate Solution at 153° C. with 0.5% Acid A 15 wt % fructose solution (according to A, above) (80% fructose, 20% glucose) in 0.5 wt % sulfuric acid was preheated first to a temperature of 75° C. and then in step c) continuously converted at a temperature of 153° C. with a residence time (relative to the heating zone) of 7 min over a test period of 68 h. Over the course of the reaction, samples were taken regularly and the composition was analyzed by means of HPLC. FIG. 6 shows the results obtained with respect to fructose conversion, selectivities and carbon balance.

Throughout the experiment, the composition of the product mixture was constant. The fructose conversion (8) was approximately 20%, the HMF selectivity (7) approximately 80% and the carbon balance (6) 98%. The 2% missing in the carbon balance consisted of analytically unrecognized intermediates and byproducts, such as, for example, soluble and insoluble humic substances.

Figure 7:
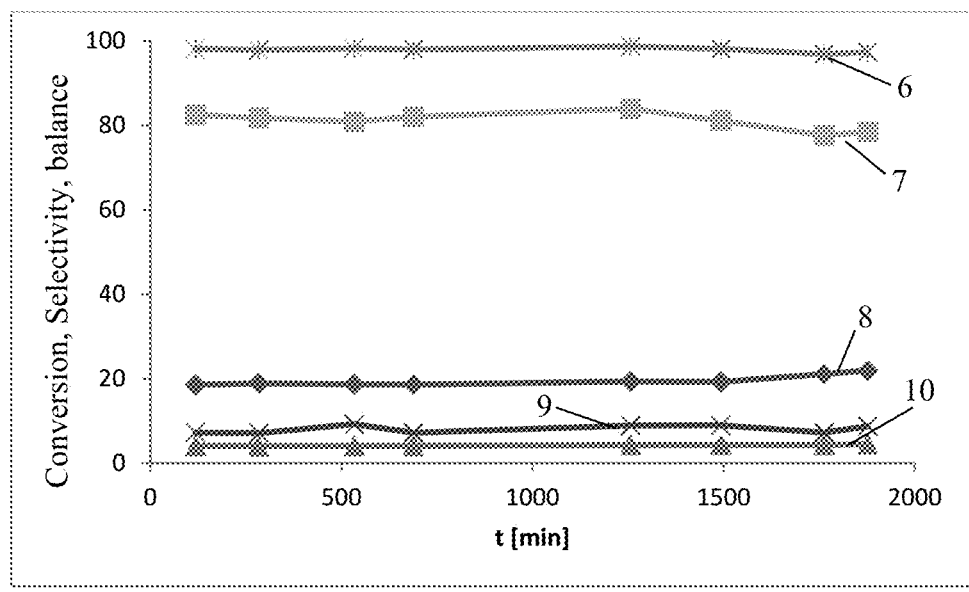
FIG. 7 shows the course of the reaction in Example 4 with 25 wt % carbohydrate, 0.75 wt % sulfuric acid, 150° C., with a residence time of 6 min and with the carbon balance (6), HMF selectivity (7), fructose turnover (8), formic acid (9), levulinic acid (10).

Example 4: HMF Synthesis with 25% Carbohydrate Solution at 150° C. with 0.75% Acid A 25 wt % fructose solution (according to A, above) (80% fructose, 20% glucose) in 0.75 wt % sulfuric acid was first preheated to 80° C. and then, in step c), continuously converted at a temperature of 150° C. with a residence time (relative to the heating zone) of 6 min over a test period of 31 h. Over the course of the reaction, samples were taken regularly and the composition was analyzed by means of HPLC. FIG. 7 shows the results obtained with respect to fructose conversion, selectivities and carbon balance.

Throughout the experiment, the composition of the product mixture was constant. The fructose conversion (8) was approximately 19.5%, the HMF selectivity (7) approximately 81% and the carbon balance (6) 98%. The 2% missing in the carbon balance consisted of analytically unrecognized intermediates and byproducts, such as, for example, soluble and insoluble humic substances.

Figure 8:
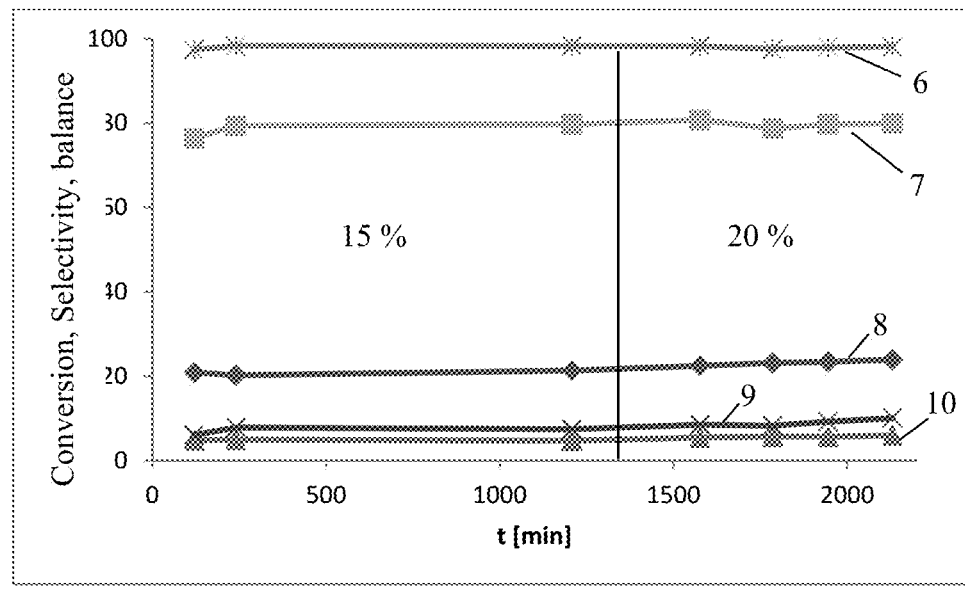
FIG. 8 shows the course of the reaction in Example 5 with 15 wt % carbohydrate (after 23 h increased to 20 w % carbohydrate), 1.0 wt % sulfuric acid, 140° C., with a residence time of 9 min and with the carbon balance (6), HMF selectivity (7), fructose turnover (8), formic acid (9), levulinic acid (10).

Example 5: HMF Synthesis with 15 (20) % Carbohydrate Solution at 140° C. with 1.0% Acid A 15 wt % fructose solution (according to A, above) (80% fructose, 20% glucose) in 1.0 wt % sulfuric acid was first preheated to 75° C. and then, in step c), continuously converted at a temperature of 140° C. with a residence time (relative to the heating zone) of 9 min over a test period of 23 h. After 23 h, the carbohydrate concentration in the feed was increased to 20 wt % and the reaction continued for another 12 h under otherwise unchanged conditions. Over the course of the reaction, samples were taken regularly and the composition was analyzed by means of HPLC. FIG. 8 shows the results obtained with respect to fructose conversion, selectivities and carbon balance.

Throughout the experiment, the composition of the product mixture was constant. The fructose conversion (8) was approximately 19.5%, the HMF selectivity (7) approximately 81% and the carbon balance (6) 8%. The 2% missing in the carbon balance consisted of analytically unrecognized intermediates and byproducts, such as, for example, soluble and insoluble humic substances.

Example 6: Continuous Separation of the HMF-Containing Product Mixture in a Two-Stage Chromatography Process I) Separation of an HMF Fraction in a First Stage and Separation of the Remaining Fractions in a Second Stage A product mixture obtained in step d) was adjusted to a dry matter content of 17 wt %. The product mixture comprised 7.8 wt % of HMF, 1.8 wt % of levulinic acid, <0.1 wt % of formic acid, 63.9 wt % of fructose, 22.5 wt % of glucose and 4 wt % acid, and is continuously separated into four fractions in step e) in a two-step chromatography method at 60° C.

Figure 10:
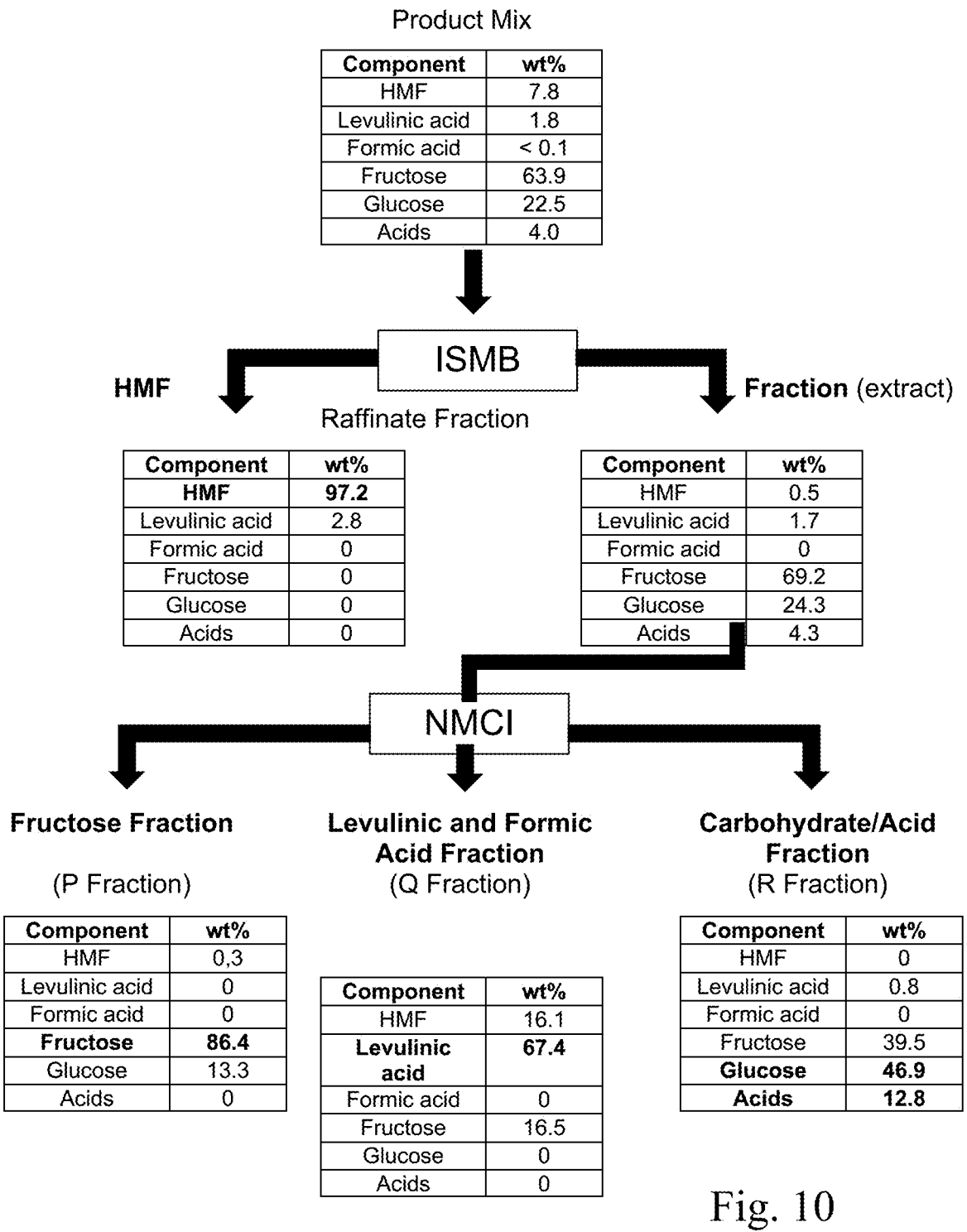
FIG. 10 shows schematically the performance of a two-stage chromatographic separation of an HMF-containing product mixture with low dry matter content in an HMF fraction (extract), a fructose fraction (P fraction), a levulinic and formic acid fraction (Q fraction) and a carbohydrate/acid fraction (R fraction). ISMB=Improved Simulated Moving Bed, NMCI=New MCI.

In the first step, the product mixture passes by means of an ISMB system to 50 l of Diaion UBK 530 chromatography resin (Mitsubishi Chemical) in Et form with water as the eluent and a water/product mixture ratio of 1.84 and separated into an HMF fraction (extract) and a raffinate fraction (FIG. 10).

The following recovery rates were obtained for the HMF fraction (based on the respective content of the product mixture fed from step d): HMF: 93.9%, levulinic acid: 12.0%, formic acid: 0.0%, fructose: 0.0%, glucose: 0.0%, acid: 0.0%.

The raffinate fraction then, after concentration in the second step, passes through a NMCI system of 141 l of Diaion UBK 530 chromatography resin in $H^+$ form with water as the eluent and a water/product mixture ratio of 4.51 and separated into a fructose fraction (P Fraction), a levulinic and formic acid fraction (Q fraction), and a carbohydrate/acid fraction (R fraction) (FIG. 10).

The following recovery rates were obtained for the fructose fraction (based on the respective content of the product mixture fed from step d): HMF: 2.0%, levulinic acid: 0.0%, formic acid: 0.0%, fructose: 80.3%, glucose: 35.2%, acid: 0.0%.

The following recovery rates were obtained for the levulinic and formic acid fractions (based on the respective content of the product mixture fed from step d): HMF: 4.0%, levulinic acid: 73.7%, formic acid: 0.0%, fructose: 0.5%, glucose: 0.0%, acid: 0.0%.

The following recovery rates were obtained for the carbohydrate/acid fraction (based on the respective content of the product mixture fed from step d): HMF: 0.0%, levulinic acid: 14.4%, formic acid: 0.0%, fructose: 19.2%, glucose: 64.0%, acid: 100.0%.

II) Separation of a Carbohydrate/Acid Fraction in a First Stage and Separation of the Remaining Fractions in a Second Stage A product mixture obtained in step d) was adjusted to a dry matter content of 17 wt %. The product mixture comprised 7.8 wt % of HMF, 1.8 wt % of levulinic salts, <0.1 wt % of formic acid, 63.9 wt % of fructose, 22.5 wt % of glucose and 4 wt % salts, and is continuously separated into four fractions in step e) in a two-step chromatography method at 60° C.

In the first step, the feed passes through an ISMB system of 135 l of Diaion UBK 530 chromatography resin (Mitsubishi Chemical) in $H^+$ form with water as the eluent and a water/product mixture ratio of 3.111 and separated into a carbohydrate/acid fraction (raffinate) and an extract fraction (FIG. 11).

The following recovery rates were obtained for the carbohydrate/acid fraction (based on the respective content of the product mixture fed from step d): HMF: 4.0%, levulinic acid: 0.0%, formic acid: 0.0%, fructose: 15.1%, glucose: 43.1%, acid: 95.9%.

The extract fraction then, after concentration in the second step, passes through a NMCI system of 190 l of Diaion UBK 530 chromatography resin in $H^+$ form with water as the eluent and a water/product mixture ratio of 7.49 and separated into the levulinic and formic acids fraction (P fraction), the HMF fraction (Q fraction) and the fructose fraction (R fraction) (FIG. 11).

The following recovery rates were obtained for the levulinic and formic acid fractions (based on the respective content of the product mixture fed from step d): HMF: 6.9%, levulinic acid: 79.0%, formic acid: 0.0%, fructose: 0.0%, glucose: 0.0%, acid: 0.0%.

The following recovery rates were obtained for the HMF fraction (based on the respective content of the product mixture fed from step d): HMF: 82.2%, levulinic acid: 0.0%, formic acid: 0.0%, fructose: 0.0%, glucose: 0.0%, acid: 1.3%.

The following recovery rates were obtained for the fructose fraction (based on the respective content of the product mixture fed from step d): HMF: 6.9%, levulinic acid: 21.0%, formic acid: 0.0%, fructose: 84.9%, glucose: 57.0%, acid: 2.8%.

III) Separation of an HMF Fraction in a First Stage and Separation of the Femaining Fractions in a Second Stage A product mixture obtained in step d) was adjusted to a dry substance content of 55 wt %. The product mixture comprised 7.6 wt % of HMF, 1.7 wt % of levulinic salts, <0.1 wt % of formic acid, 62.8 wt % of fructose, 23.3 wt % of glucose and 4.6 wt % of salts, and is continuously separated into four fractions in step e) in a two-step chromatography method at 60° C.

In the first step, the product mixture passes by means of an ISMB system to 14 l of Diaion UBK 530 chromatography resin (Mitsubishi Chemical) in Et form with water as the eluent and a water/product mixture ratio of 1.84 and separated into an HMF fraction (extract) and a raffinate fraction (FIG. 12).

The following recovery rates were obtained for the HMF fraction (based on the respective content of the product mixture fed from step d): HMF: 87.5%, levulinic acid: 12.7%, formic acid: 0.0%, fructose: 0.0%, glucose: 0.0%, acid: 0.0%.

The raffinate fraction then, after concentration in the second step, passes through a NMCI system of 104 l of Diaion UBK 530 chromatography resin in $H^+$ form with water as the eluent and a water/product mixture ratio of 5.42 and separated into a fructose fraction (P Fraction), a levulinic and formic acid fraction (Q fraction), and a carbohydrate/acid fraction (R fraction) (FIG. 12).

The following recovery rates were obtained for the fructose fraction (based on the respective content of the product mixture fed from step d): HMF: 1.8%, levulinic acid: 0.0%, formic acid: 0.0%, fructose: 89.4%, glucose: 56.4%, acid: 0.0%.

The following recovery rates were obtained for the levulinic and formic acid fractions (based on the respective content of the product mixture fed from step d): HMF: 0.7%, levulinic acid: 74.8%, formic acid: 0.0%, fructose: 0.1%, glucose: 0.0%, acid: 2.2%.

The following recovery rates were obtained for the carbohydrate/acid fraction (based on the respective content of the product mixture fed from step d): HMF: 9.9%, levulinic acid: 13.3%, formic acid: 0.0%, fructose: 10.6%, glucose: 43.8%, acid: 97.9%.

IV) Separation of a Carbohydrate/Acid Fraction in a First Stage and Separation of the Remaining Fractions in a Second Stage A product mixture obtained in step d) was adjusted to a dry substance content of 55 wt %. The product mixture comprised 7.6 wt % of HMF, 1.7 wt % of levulinic salts, <0.1 wt % of formic acid, 62.8 wt % of fructose, 23.3 wt % of glucose and 4.6 wt % of salts, and is continuously separated into four fractions in step e) in a two-step chromatography method at 60° C.

In the first step, the feed passes through an ISMB system of 39 l of Diaion UBK 530 chromatography resin (Mitsubishi Chemical) in $H^+$ form with water as the eluent and a water/product mixture ratio of 3.67 and separated into a carbohydrate/acid fraction (raffinate) and an extract fraction (FIG. 13).

The following recovery rates were obtained for the carbohydrate/acid fraction (based on the respective content of the product mixture fed from step d): HMF: 6.4%, levulinic acid: 0.0%, formic acid: 0.0%, fructose: 10.4%, glucose: 37.3%, acid: 99.1%.

The extract fraction then, after concentration in the second step, passes through a NMCI system of 105 l of Diaion UBK 530 chromatography resin in $H^+$ form with water as the eluent and a water/product mixture ratio of 7.49 and separated into the levulinic and formic acids fraction (P fraction), the HMF fraction (Q fraction) and the fructose fraction (R fraction) (FIG. 13).

The following recovery rates were obtained for the levulinic and formic acid fractions (based on the respective content of the product mixture fed from step d): HMF: 1.4%, levulinic acid: 82.2%, formic acid: 0.0%, fructose: 0.3%, glucose: 0.2%, acid: 0.0%.

The following recovery rates were obtained for the HMF fraction (based on the respective content of the product mixture fed from step d): HMF: 76.4%, levulinic acid: 0.0%, formic acid: 0.0%, fructose: 0.0%, glucose: 0.0%, acid: 0.0%.

The following recovery rates were obtained for the fructose fraction (based on the respective content of the product mixture fed from step d): HMF: 16.1%, levulinic acid: 18.2%, formic acid: 0.0%, fructose: 89.7%, glucose: 62.8%, acid: 1.0%.

Example 7: Oxidation of an HMF Solution from the Process According to the Invention A product mixture obtained from a 10% wt % fructose solution (96% fructose, 2.3% glucose, 1.7% residual saccharides) was separated by chromatography. The resulting HMF fraction has a purity of 98.1 g/100 g dry matter and was concentrated to a concentration of 0.4 mol/l and converted to 2.5-furandicarboxylic acid (FDCA) in an oxidation experiment under the following reaction conditions.

Figure 9:
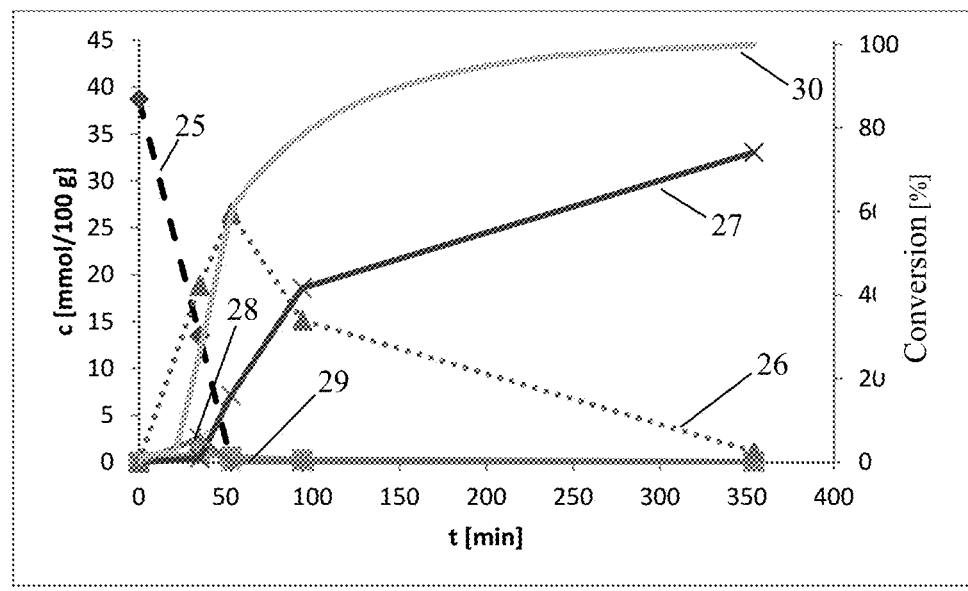
FIG. 9 shows the results from an oxidation of an HMF solution from the process according to the invention. HMF=5-hydroxymethylfurfural (25), HMCA=5-hydroxymethyl-2-furancarboxylic acid (29), FFCA=5-formyl-2-furancarboxylic acid (26), FDCA=2.5-furandicarboxylic acid (27), FDC=2, 5-furandicarboxaldehyde (28), conversion from NaOH curve (30).

Batch size=500 g
$C_{HMF}$=0.4 mol/l
$C_{catalyst}$=5.94 g/l (based on the dry matter of the catalyst)
Catalyst=5% Pt/1% Bi/C (Degussa/Evonik)
T=60° C.
pH=9.0
Titrant=16 wt % NaOH
Pressure=atmospheric
$O_2$=500 ml/min Samples were taken regularly, and these were analyzed for their composition by means of HPLC (BIORAD, Aminex 87-H, 5 mmol/l $H_2SO_4$, 50° C.). The test results are shown in FIG. 9.

It was possible to fully convert the HMF (25) that was used. The free 2.5-furandicarboxylic acid (27) from the oxidized solution was then precipitated, dried and analyzed by lowering the pH with hydrochloric acid. The purity of the resulting FDCA was 98.2%.

The invention claimed is:

1. A method for production of 5-hydroxymethylfurfural (HMF) in a continuous process comprising:
   a) providing an aqueous fructose-containing starting solution and at least one homogeneous acidic catalyst;
   b) mixing of the aqueous fructose-containing starting solution and the at least one homogeneous acid catalyst to obtain a reaction solution having a carbohydrate content ranging from 5 wt % to 50 wt % (dry matter carbohydrate relative to a total weight of the reaction solution) and a fructose content ranging from 40 wt % to 100 wt % (dry matter fructose relative to the dry matter carbohydrate);
   c) feeding of the reaction solution obtained in step b) into a continuous reactor system and conversion of the fructose present in the reaction solution to HMF at a temperature ranging from 80° C. to 165° C. to obtain an HMF-containing product mixture while adjusting for a fructose conversion ranging from 1 mol % to 40 mol %;

d) adjusting the product mixture to a temperature ranging from 20° C. to 80° C.; and e) purifying the product mixture obtained in step d) by using chromatography to separate at least four fractions comprising an HMF fraction, a carbohydrate/acid fraction, a fructose fraction and a levulinic and formic acid fraction.

2. The method of claim 1, wherein, in step a), an aqueous fructose-containing starting solution, an aqueous returned fructose-containing fraction and at least one homogeneous acidic catalyst are provided, wherein, in step b), the aqueous fructose-containing starting solution, the aqueous returned fructose-containing fraction and the at least one homogeneous acidic catalyst are mixed to obtain a reaction solution having a carbohydrate content ranging from 5 wt % to 50 wt % (dry matter carbohydrate relative to the total weight of the reaction solution) and a fructose content ranging from 40 wt % to 100 wt % (dry matter, fructose in relation to the dry matter of the carbohydrates), and wherein the fructose fraction obtained in step e) or step f) is continuously returned at least partially to step a).

3. The method of claim 1, wherein the reaction solution obtained in step b) is preheated to a temperature ranging from 80° C. to 165° C.

4. The method of claim 1, wherein, before step b), at least one of the components provided in step a) is preheated to a temperature ranging from 80° C. to 165° C.

5. The method of claim 1, wherein a concentration of the at least one homogeneous acid catalyst is 0.5 wt % to 5 wt % (wt % in relation to the total weight of reaction solution).

6. The method of claim 1, wherein the at least one homogeneous acidic catalyst is selected from sulfuric acid, hydrochloric acid, phosphoric acid, aliphatic or aromatic carboxylic acids and aliphatic or aromatic sulfonic acids.

7. The method of claim 1, wherein no organic solvents are used in the process.

8. The method of claim 1, wherein the conversion of the fructose to HMF in step c) takes place during a period ranging from 0.1 to 20 min.

9. The method of claim 1, wherein a HMF selectivity in step c) ranges from 60 mol % to 100 mol %.

10. The method of claim 1, wherein the chromatography is a chromatography on ion exchange resins.

11. The method of claim 1, wherein in the chromatography, in particular the chromatography on ion exchange resins, in step e) is a Simulated Moving Bed method (SMB), a Sequential Simulated Moving Bed method (SSMB), an Improved Simulated Moving Bed Method (ISMB) or a New MCI Method (NMCI).

12. The method of claim 1, wherein the chromatography in step e) is a multi-step process.

13. The method of claim 1, wherein the chromatography in step e) is a chromatography on cation exchange resins.

14. The method of claim 13, wherein the chromatography on cation exchange resins in step e) is carried out using a cation exchange resin in $H^+$ form.

15. The method of claim 1, wherein the chromatography is preceded by a filtration of the product mixture, a decolorization and/or a purification of the product mixture via activated carbon.

16. The method of claim 1, wherein step e) is carried out at a temperature ranging from 40° C. to 80° C.

17. The method of claim 1, wherein the product mixture obtained in step d) before step e) is concentrated to a dry matter content ranging from 20 wt % to 50 wt %.

18. The method of claim 1, wherein the carbohydrate/acid fraction separated in step e) or obtained in step f) is used for production of ethanol.

19. The method of claim 1, wherein the levulinic and formic acid fraction separated in step e) or obtained in step f) is used for isolation of levulinic and formic acid.

20. The method of claim 1, wherein the HMF separated in step e) or in step f) is oxidized to 2.5-furandicarboxylic acid (FDCA) directly and without further purification in another step.

* * * * *